US012702833B2

(12) United States Patent
Rockley et al.

(10) Patent No.: US 12,702,833 B2
(45) Date of Patent: Aug. 11, 2026

(54) HEAD WORN APPARATUSES FOR VISION THERAPY

(71) Applicant: i-Lumen Scientific, Inc., Bloomington, MN (US)

(72) Inventors: Paul Rockley, Corona Del Mar, CA (US); James R. Chiapetta, Delano, MN (US); Thomas W. Harold, Prior Lake, MN (US); Michael Ashker, Gold River, CA (US)

(73) Assignee: i-Lumen Scientific, Inc., Bloomington, MN (US)

( * ) Notice: Subject to any disclaimer, the term of this patent is extended or adjusted under 35 U.S.C. 154(b) by 436 days.

(21) Appl. No.: 17/718,026

(22) Filed: Apr. 11, 2022

(65) Prior Publication Data

US 2022/0305265 A1 Sep. 29, 2022

Related U.S. Application Data

(63) Continuation of application No. 16/697,689, filed on Nov. 27, 2019, now Pat. No. 11,305,118.

(60) Provisional application No. 62/774,093, filed on Nov. 30, 2018.

(51) Int. Cl.
*A61N 1/00* (2006.01)
*A61N 1/04* (2006.01)
*A61N 1/36* (2006.01)

(52) U.S. Cl.
CPC ....... *A61N 1/36046* (2013.01); *A61N 1/0408* (2013.01); *A61N 1/0484* (2013.01); *A61N 1/36014* (2013.01)

(58) Field of Classification Search
None
See application file for complete search history.

(56) References Cited

U.S. PATENT DOCUMENTS 2,283,752 A 5/1942 Gonsett
2,527,947 A 10/1950 Loos
2,760,483 A 8/1956 Tassicker
3,376,870 A * 4/1968 Yamamoto ......... A61N 1/36021 600/27
3,669,119 A 6/1972 Symmes
D246,529 S 11/1977 Willard
(Continued)

FOREIGN PATENT DOCUMENTS

CN 1096460 A 12/1994
DE 202012003100 U1 10/2012
(Continued)

OTHER PUBLICATIONS

Chlaihawi et al; "Development of Printed and Flexible Dry ECG Electrodes", Sensing and Bio-Sensing Research, vol. 20, pp. 9-15, 2018.

(Continued)

*Primary Examiner* — William J Levicky
*Assistant Examiner* — Anant A Gupta
(74) *Attorney, Agent, or Firm* — Fox Rothschild LLP

(57) ABSTRACT

Systems, devices, and methods for use in delivering stimulation to the head of a patient, including examples directed to delivering electrical or other stimulation to the eye of the patient. In some examples eyepieces or eyepatches are configured to deliver electrical or other stimulus to the eye of a patient by being worn on the face of the patient.

29 Claims, 25 Drawing Sheets

(56) References Cited

U.S. PATENT DOCUMENTS 4,162,542 A 7/1979 Frank
D280,670 S 9/1985 Fireman
4,551,149 A 11/1985 Scairra
4,614,193 A 9/1986 Liss et al.
4,628,933 A 12/1986 Michelson
4,664,117 A 5/1987 Beck
4,712,558 A 12/1987 Kidd et al.
4,979,811 A 12/1990 Boyer
5,024,223 A 6/1991 Chow
5,109,844 A 5/1992 De Juan et al.
5,147,284 A 9/1992 Fedorov et al.
5,154,174 A 10/1992 Hawlina
5,193,540 A 3/1993 Schulman et al.
5,263,200 A 11/1993 Miller
5,522,864 A 6/1996 Wallace et al.
5,556,423 A 9/1996 Chow et al.
5,597,381 A 1/1997 Rizzo, III
5,643,330 A 7/1997 Holsheimer et al.
5,836,996 A 11/1998 Doorish
5,843,147 A 12/1998 Testerman et al.
5,865,839 A 2/1999 Doorish
5,873,901 A 2/1999 Wu et al.
5,895,415 A 4/1999 Chow et al.
5,935,155 A 8/1999 Humayun et al.
5,944,747 A 8/1999 Greenberg et al.
6,007,532 A 12/1999 Netherly
D421,124 S 2/2000 Yavitz
6,035,236 A 3/2000 Jarding et al.
D425,623 S 5/2000 Funk
D429,817 S 8/2000 Banks
6,101,411 A 8/2000 Newsome
6,131,208 A 10/2000 Banks
6,154,671 A 11/2000 Parel et al.
D440,660 S 4/2001 Sternberg
6,230,057 B1 5/2001 Chow et al.
D444,561 S 7/2001 Stein
6,275,735 B1 8/2001 Jarding et al.
6,282,449 B1 8/2001 Kamerling et al.
6,306,075 B1 10/2001 Shadduck
6,324,429 B1 11/2001 Shire et al.
6,389,317 B1 5/2002 Chow et al.
6,400,989 B1 6/2002 Eckmiller
6,408,211 B1 6/2002 Powell
6,424,864 B1 7/2002 Matsuura
6,442,431 B1 8/2002 Veraart et al.
6,458,157 B1 10/2002 Suaning
6,515,227 B1 2/2003 Massey et al.
6,611,716 B2 8/2003 Chow et al.
6,755,530 B1 6/2004 Loftus et al.
6,792,314 B2 9/2004 Byers et al.
6,976,998 B2 12/2005 Rizzo et al.
6,990,377 B2 1/2006 Gliner et al.
7,001,608 B2 2/2006 Fishman et al.
7,003,354 B2 2/2006 Chow et al.
7,006,873 B2 2/2006 Chow et al.
7,031,776 B2 4/2006 Chow et al.
7,037,943 B2 5/2006 Peyman
7,043,308 B2 5/2006 Cohen
7,047,080 B2 5/2006 Palanker et al.
7,058,455 B2 6/2006 Huie, Jr. et al.
7,067,327 B2 6/2006 Wu et al.
7,130,693 B1 10/2006 Montalbo
7,139,612 B2 11/2006 Chow et al.
7,146,209 B2 12/2006 Gross et al.
7,147,865 B2 12/2006 Fishman et al.
7,158,834 B2 1/2007 Paul, Jr.
7,158,836 B2 1/2007 Suzuki
7,248,928 B2 7/2007 Yagi
7,251,528 B2 7/2007 Harold
7,306,621 B1 12/2007 Halla et al.
7,321,796 B2 1/2008 Fink et al.
7,337,008 B2 2/2008 Terasawa et al.
7,398,124 B2 7/2008 Fujikado et al.
7,400,021 B2 7/2008 Wu et al.
7,447,547 B2 11/2008 Palanker
7,447,548 B2 11/2008 Eckmiller
7,458,456 B2 12/2008 Hogan et al.
7,556,621 B2 7/2009 Palanker et al.
7,877,148 B2 1/2011 Chowdhury et al.
7,883,535 B2 2/2011 Cantin et al.
7,974,699 B2 7/2011 Tano et al.
7,979,134 B2 7/2011 Chow et al.
7,981,062 B2 7/2011 Chow et al.
8,000,804 B1 8/2011 Wessendorf et al.
8,039,445 B2 10/2011 Behar-Cohen et al.
8,070,688 B2 12/2011 Livne et al.
8,190,266 B2 5/2012 Ameri et al.
8,197,539 B2 6/2012 Nasiatka et al.
8,260,428 B2 9/2012 Fink et al.
8,265,764 B2 9/2012 Tano et al.
8,306,626 B2 11/2012 Chow et al.
8,377,120 B2 2/2013 Lipshitz et al.
8,396,561 B2 3/2013 Pezaris et al.
8,396,562 B2 3/2013 Ameri et al.
8,398,692 B2 3/2013 Deisseroth et al.
8,433,417 B2 4/2013 Flood
8,478,415 B1 7/2013 Halla et al.
8,515,548 B2 8/2013 Rofougaran et al.
8,612,002 B2 12/2013 Faltys et al.
8,634,923 B2 1/2014 Sharpee et al.
8,639,345 B2 1/2014 Eipper et al.
8,691,877 B2 4/2014 Yun et al.
8,700,167 B2 4/2014 Sabel
8,725,266 B2 5/2014 Olson et al.
8,731,683 B2 5/2014 Lindenthaler
8,734,513 B2 5/2014 Wu et al.
8,771,349 B2 7/2014 Schachar
8,788,041 B2 7/2014 Yun et al.
8,801,942 B2 8/2014 Scorsone et al.
8,824,156 B2 9/2014 Tai et al.
8,852,290 B2 10/2014 Rowley et al.
8,864,805 B2 10/2014 Deisseroth et al.
8,868,202 B2 10/2014 Della Santina et al.
8,903,495 B2 12/2014 Greenberg et al.
8,909,340 B2 12/2014 Yun
8,918,186 B2 12/2014 Tiedtke
8,918,188 B2 12/2014 Tiedtke
8,972,004 B2 3/2015 Simon et al.
9,002,463 B2 4/2015 Tiedtke
9,037,251 B2 5/2015 Narayan et al.
9,037,252 B2 5/2015 Tiedtke
9,037,255 B2 5/2015 Rocke et al.
9,078,743 B2 7/2015 Tai et al.
9,079,042 B2 7/2015 Tiedtke et al.
9,125,734 B2 9/2015 Keller et al.
9,144,608 B2 9/2015 Olson et al.
9,162,060 B2 10/2015 Wrobel et al.
9,162,061 B2 10/2015 Barnes
9,180,309 B2 11/2015 Nirenberg et al.
9,186,523 B1 11/2015 Zolli
9,187,745 B2 11/2015 Deisseroth et al.
9,199,080 B2 12/2015 Gekeler et al.
9,220,634 B2 12/2015 Nirenberg
9,220,894 B1 12/2015 Zhu
9,233,026 B2 1/2016 Ziemeck et al.
9,233,258 B2 1/2016 Simon et al.
9,242,067 B2 1/2016 Shore et al.
9,302,103 B1 4/2016 Nirenberg
9,322,713 B2 4/2016 Narayan et al.
9,326,887 B2 5/2016 Yun
9,339,650 B2 5/2016 Rezai et al.
9,345,568 B2 5/2016 Cho et al.
9,370,348 B2 6/2016 Tally et al.
9,381,355 B2 7/2016 Chraiche et al.
9,403,001 B2 8/2016 Simon et al.
9,452,289 B2 9/2016 Chichilnisky et al.
9,456,836 B2 10/2016 Boling et al.
9,468,760 B1 10/2016 Lin
9,498,380 B2 11/2016 Berdahl et al.
9,630,013 B2 4/2017 Bachinski et al.
9,636,212 B2 5/2017 Tiedtke et al.
9,682,232 B2 6/2017 Shore et al.
9,687,652 B2 6/2017 Franke et al.
9,697,746 B2 7/2017 Barnes et al.

(56) References Cited

U.S. PATENT DOCUMENTS

| | | | |
|---|---|---|---|
| 9,737,710 | B2 | 8/2017 | Fan |
| 9,737,711 | B2 | 8/2017 | Twyford et al. |
| 9,789,312 | B2 | 10/2017 | Fukuma et al. |
| 9,795,787 | B2 | 10/2017 | Cho et al. |
| 9,821,003 | B2 | 11/2017 | Yun |
| 9,821,159 | B2 | 11/2017 | Ackermann et al. |
| 9,844,459 | B2 | 12/2017 | Badawi |
| 9,867,988 | B2 | 1/2018 | Fink et al. |
| 9,884,180 | B1 | 2/2018 | Ho et al. |
| 9,895,529 | B2 | 2/2018 | Tiedtke |
| 9,925,373 | B2 | 3/2018 | Nirenberg |
| 9,931,506 | B2 | 4/2018 | Chung et al. |
| 9,937,346 | B2 | 4/2018 | Lineaweaver et al. |
| 9,950,153 | B2 | 4/2018 | Wagner et al. |
| 9,956,425 | B2 | 5/2018 | Peyman |
| 9,962,540 | B2 | 5/2018 | Picaud et al. |
| 9,962,558 | B2 | 5/2018 | Peyman |
| 9,980,388 | B2 | 5/2018 | Tai et al. |
| 9,990,861 | B2 | 6/2018 | Chichilnisky et al. |
| 10,010,364 | B2 | 7/2018 | Harrington |
| 10,071,251 | B2 | 9/2018 | Bachinski et al. |
| 10,112,048 | B2 | 10/2018 | Franke et al. |
| 10,129,647 | B2 | 11/2018 | Seo et al. |
| 10,347,050 | B1 | 7/2019 | Wang et al. |
| 11,035,118 | B2 | 6/2021 | Gamarekian et al. |
| 2003/0158588 | A1 | 8/2003 | Rizzo et al. |
| 2003/0233135 | A1 | 12/2003 | Yee |
| 2003/0233137 | A1 | 12/2003 | Paul, Jr. |
| 2004/0106965 | A1 | 6/2004 | Chow |
| 2004/0176820 | A1 | 9/2004 | Paul, Jr. |
| 2005/0004625 | A1 | 1/2005 | Chow |
| 2005/0049578 | A1 | 3/2005 | Tu et al. |
| 2005/0137649 | A1 | 6/2005 | Paul, Jr. |
| 2006/0142818 | A1 | 6/2006 | Chow et al. |
| 2007/0093877 | A1 | 4/2007 | Beecham et al. |
| 2007/0179564 | A1 | 8/2007 | Harold |
| 2008/0171929 | A1 | 7/2008 | Katims |
| 2008/0194531 | A1 | 8/2008 | Steer et al. |
| 2009/0217938 | A1 | 9/2009 | Rabe et al. |
| 2009/0287276 | A1 | 11/2009 | Greenberg et al. |
| 2011/0081333 | A1 | 4/2011 | Shantha et al. |
| 2012/0123501 | A1 | 5/2012 | Greenberg et al. |
| 2013/0053733 | A1 | 2/2013 | Korb et al. |
| 2013/0066396 | A1 | 3/2013 | Gekeler et al. |
| 2013/0184782 | A1 | 7/2013 | Eipper et al. |
| 2014/0257433 | A1 | 9/2014 | Ackermann et al. |
| 2014/0277435 | A1 | 9/2014 | Gefen |
| 2014/0324147 | A1 | 10/2014 | Wagner |
| 2015/0039067 | A1 | 2/2015 | Greenberg et al. |
| 2015/0209174 | A1 | 7/2015 | Abreu |
| 2016/0051439 | A1 | 2/2016 | Brown et al. |
| 2016/0317474 | A1 | 11/2016 | Aung et al. |
| 2016/0374594 | A1* | 12/2016 | Garcia Molina ...... A61B 5/163 600/558 |
| 2017/0266445 | A1 | 9/2017 | O'Clock |
| 2018/0064935 | A1 | 3/2018 | Leonhardt et al. |
| 2018/0185651 | A1* | 7/2018 | Astrom .............. A61N 1/36185 |
| 2018/0228237 | A1 | 8/2018 | Zhang et al. |
| 2018/0318585 | A1 | 11/2018 | Pfeifer |
| 2018/0318586 | A1 | 11/2018 | Salazar |
| 2019/0143116 | A1 | 5/2019 | Mowery et al. |
| 2019/0223747 | A1 | 7/2019 | Chou |
| 2020/0391029 | A1 | 12/2020 | Mullins et al. |

FOREIGN PATENT DOCUMENTS

| | | | | |
|---|---|---|---|---|
| EP | 1985332 | A1 | 10/2008 | |
| GB | 2246709 | A | 2/1992 | |
| WO | 2006086452 | A1 | 8/2006 | |
| WO | 2013124141 | A1 | 8/2013 | |
| WO | 2015095257 | A2 | 6/2015 | |
| WO | 2016089751 | A1 | 6/2016 | |
| WO | WO-2017048731 | A1 * | 3/2017 | ......... A61N 1/36031 |
| WO | 2017064500 | A1 | 4/2017 | |
| WO | 2018013835 | A1 | 1/2018 | |
| WO | WO-2018089506 | A1 * | 5/2018 | ............. G01R 27/26 |
| WO | 2018129351 | A1 | 7/2018 | |
| WO | 2018208009 | A1 | 11/2018 | |

OTHER PUBLICATIONS

2019 World Congress Eye and Chip Speaker Abstracts, pp. 20-54, 2019.

Gall et al; Alternating Current Stimulation for Vision Restoration after Optic Nerve Damage: A Randomized Clinical Trial, PLOS One, pp. 1-13, 2016, accessed Nov. 12, 2018.

Chow et al; "The Artificial Silicon Retina in Retinitis Pigmentosa Patients", Trans Am Ophthalmol Soc., vol. 108, pp. 120-154, 2010.

Dawson et al; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al; Phosphene Thresholds Elicited by Trasncorneal Electrical Stimulation in Healthy Subjects and Patients with Retinal Disease, Investigative Ophthamology and Visual Science, vol. 53, No. 12, pp. 7440-7448, 2012, accessed on Sep. 20, 2018.

Schatz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC.

Stauffer et al; "Skin Conformal Polymer Electrodes for Clinical ECG and EEG Recordings," Advanced Healthcare Materials pp. 1-10, 2018.

Manthey et al; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.

Invite to Pay Additional Fees dated Dec. 17, 2019 for International Application No. PCT/US2019/054028.

International search Report and Written Opinion dated Jul. 10, 2020 for International Application No. PCT/US2020/027438.

Invite to Pay Additional Fees dated Aug. 31, 2020 for International Application No. PCT/US2020/037458.

Invite to Pay Additional Fees dated Feb. 14, 2020 for International Application No. PCT/US2019/063580.

* cited by examiner 110
112
100
102
114

616
622
610
624

610

622
624
610
614
600
616
620
612

830
832
834
836

830
832
834
836

922
926
930
928
920
924
934
932

930
902
906
908
900
904

946
948
944
942
940

948

960
964
968
950
962
966

984
988
986
982
980

HEAD WORN APPARATUSES FOR VISION THERAPY

CROSS REFERENCE TO RELATED APPLICATIONS

The present application is a continuation of U.S. patent application Ser. No. 16/697,689, filed Nov. 27, 2019 titled HEAD WORN APPARATUSES FOR VISION THERAPY, which claims the benefit of and priority to U.S. Provisional Patent Application No. 62/774,093, filed Nov. 30, 2018, titled HEAD WORN APPARATUSES FOR VISION THERAPY, the disclosure of each is incorporated herein by reference.

FIELD

The present invention relates generally to the field of delivery of therapeutic energy for treatment of conditions around the head. More particularly, the present invention is directed to systems and methods adapted to deliver energy to the eye and/or tissue surrounding the eye.

BACKGROUND

Therapy to prevent or reverse diseases of the eye is of great interest. As life expectancy expands, more and more of the population is at risk for age related macular degeneration (AMD). Meanwhile, smaller populations of young patients suffer from a variety of maladies that affect the retina and other structures of the eye. A wide variety of other vision disorders exist which can lead to partial or total blindness. There is a continuing demand for new and alternative systems and methods to treat such disorders including by preventing, arresting or reversing disease progress, or at least by alleviating ongoing symptoms.

A variety of proposed head worn apparatuses have been disclosed for the delivery of electrical stimulus (sometimes referred to as microcurrent therapy) to the eye. Patches, goggles, and devices resembling glasses have been proposed. However, there remains a continuing demand for improved head worn apparatuses for delivering this promising therapy to persons afflicted with diseases of the eye.

Overview

A first illustrative and non-limiting example takes the form of a patient interface apparatus for delivery of stimulus to a portion of the head of a patient, the patient interface apparatus comprising: a first eyepiece adapted to fit over and around at least one eye of the patient; a strap to hold the first eyepiece on the head of the patient, the strap being coupled to a return electrode, wherein the return electrode is tethered to the strap for placement of the return electrode on the neck, chest, shoulder or back of the patient; wherein the first eyepiece comprises at least first and second electrodes electrically isolated from one another, the first eyepiece further comprising at least first and second electrical connectors separately coupled to the first and second electrodes.

A second illustrative and non-limiting example takes the form of a patient interface apparatus for delivery of stimulus to a portion of the head of a patient, the patient interface apparatus comprising: a first eyepiece adapted to fit over and around at least one eye of the patient; a frame to hold the first eyepiece on the head of the patient; wherein the first eyepiece comprises at least first and second electrodes electrically isolated from one another, the first eyepiece further comprising at least first and second electrical connectors separately coupled to the first and second electrodes. Further to the second non-limiting example, the frame and the first eyepiece may be linked together with a spring such that the first eyepiece flips up or down relative to the face of the patient when worn.

Additionally or alternatively to the first and second non-limiting examples, the apparatus may further comprise a port coupled to one of the frame, strap or the first eyepiece, the port comprising at least first, and second electrical connections for coupling to the first, second, and return electrodes. Additionally or alternatively to the first and second non-limiting examples, the first eyepiece includes a skin interface adapted to seal relative to the skin of the patient, further wherein the first eyepiece is adapted for delivering negative air pressure to a chamber defined by the skin of the patient and the skin interface, securing the first and second electrodes into electrical contact with the skin of the patient. Additionally or alternatively to the first and second non-limiting examples, the first eyepiece is sized and shaped to cover both eyes of the patient. Additionally or alternatively to the first and second non-limiting examples, the apparatus may further comprise a second eyepiece adapted to fit over and around at least one eye of the patient such that the first eyepiece is configured for placement over the right eye and the second eyepiece is configured for placement over the left eye, the second eyepiece comprising at least third and fourth electrodes electrically isolated from one another.

Additionally or alternatively to the first and second non-limiting examples, a system comprises an apparatus as in any of the above examples and a pulse generator for coupling to the first, second and return electrodes and configured with output circuitry adapted to: generate a first output between the first and second electrodes to test coupling of the first and second electrodes to skin of the patient; and generate a second output between at least one of the first and second electrodes and the return electrode for delivering stimulation to at least one eye of the patient. In a further non-limiting example, the pulse generator is attached to the strap and is thereby adapted as a head worn apparatus. In a still further non-limiting example, the pulse generator comprises a communications module adapted for wireless communication with at least one of a programmer for the system or a personal computing device of a patient, the personal computing device taking the form of at least one of a smartphone, a tablet, or a laptop computer.

Additionally or alternatively to the first and second non-limiting examples, a system comprising an apparatus as in any of the above examples and a pulse generator for coupling to the first, second and return electrodes and comprising an air pump adapted for providing negative pressure to the first eyepiece and output circuitry, the pulse generator adapted and configured to: generate a first output between the first and second electrodes to test coupling of the first and second electrodes to skin of the patient; and generate a second output between at least one of the first and second electrodes and the return electrode for delivering stimulation to at least one eye of the patient. In a still further example, the pulse generator is adapted to deliver stimulation in the following sequence: receive a command to start; activate the air pump to provide negative pressure to the first eyepiece; generate the first output to test coupling of the first and second electrodes to skin of the patient; determine whether the test coupling as tested is adequate and, if so, deliver the second output; or, if not, turn off and re-activate the air pump or else issue an error message.

Additionally or alternatively to the first and second non-limiting examples, the first eyepiece is adapted to rest against the orbital bones surrounding the eye. Additionally or alternatively to the first and second non-limiting examples, the first eyepiece is adapted to rest against one of the eyelids of the patient. Additionally or alternatively to the first and second non-limiting examples, the first eyepiece comprises a transparent portion allowing the patient to see through the first eyepiece while it is worn. Additionally or alternatively to the first and second non-limiting examples, the first eyepiece comprises an opaque portion blocking entry of ambient light to the eye of the patient while it is worn.

Additionally or alternatively to the first and second non-limiting examples, the first eyepiece comprises an electrochromatic portion adapted to be clear in a first state and opaque or semiopaque in a second state. Further to such an example, is a non-limiting example in the form of a method of treating a patient having an eye condition using a system comprising a pulse generator and an apparatus with the first eyepiece, the apparatus further comprising a camera, the method comprising: while a patient is wearing the apparatus, activating the first and second electrodes to deliver a first stimulation, with the electrochromatic portion in the first state as controlled by a first output of the pulse generator; after delivering the first stimulation, modifying the first output to place the electrochromatic portion in a second state; and while the patient is still wearing the apparatus and with the electrochromatic portion in the second state, capturing an image of the retina of the patient using the camera.

Additionally or alternatively to the first and second non-limiting examples, the first eyepiece comprises a screen adapted to display an image to the patient. Further to such an example, is a non-limiting example in the form of a method of treating a patient having an eye condition using a system comprising a pulse generator and an apparatus with such a first eyepiece, the apparatus further comprising a camera, the method comprising: while a patient is wearing the apparatus, activating the first and second electrodes to deliver a first stimulation; after delivering the first stimulation, displaying an object on the screen and moving the object on the screen; and capturing a plurality of images of the eye of the patient as the image is moved on the screen to test the patient's response to the first stimulation. In another method using such an example, the apparatus further comprising a camera, the method comprises: while a patient is wearing the apparatus, activating the first and second electrodes to deliver first a stimulation; and after delivering the first stimulation, performing functional vision testing on the patient using the camera and the screen.

Additionally or alternatively to the first and second non-limiting examples, the apparatus further comprises a compliant inflatable member on which the first and second electrodes are placed, the compliant inflatable member adapted to enhance contact of the first and second electrodes to the skin of the patient. Further to such an example, is a non-limiting example in the form of a method of treating a patient having an eye condition using a system comprising a pulse generator and an apparatus as in claim 22, the pulse generator having at least first and second electrical outputs and a pneumatic output, the method comprising: while a patient is wearing the apparatus, activating the pneumatic output to inflate the inflatable member to a predetermined pressure; with the inflatable member at least partly inflated, applying an electrical output to at least a pair of the first, second, and return electrodes to measure tissue contact of at least one of the first, second, and return electrodes; determining whether the tissue contact is adequate and, if not, adjusting the predetermined pressure, finding that tissue contact is adequate, and, then, delivering a stimulation using at least a pair of the first, second and return electrodes. Still further to this example, the first and second electrodes are thin film electrodes disposed on a flex circuit, the flex circuit being attached to or forming a wall of the inflatable compliant member. Additionally or alternatively to the first and second non-limiting examples, the first and second electrodes are thin film electrodes disposed on a flex circuit.

Additionally or alternatively to the first and second non-limiting examples, the apparatus defines a tissue facing side and an outward facing side, further comprising a camera on the tissue facing side for capturing images of the anatomy of a patient during use. The anatomy may be the patient's eye or a portion thereof.

Additionally or alternatively to the first and second non-limiting examples the apparatus may further comprise a light source for generating a light output to interrogate anatomy of the patient, such that the camera serves to capture reflectance from patient anatomy when the light source is in use. Further to such an example, is a non-limiting example in the form of a system comprising the apparatus and a pulse generator, the pulse generator comprising a plurality of outputs for separately coupling to the first, second and return electrodes, the camera, and the light source, the pulse generator adapted to use the light source to illuminate a portion of the eye of a patient and the camera to capture images while the light source is in use, thereby identifying pulsatile blood flow, blockage of blood flow, features of the retina, and/or an estimate of pressure inside the eye.

Additionally or alternatively, a system may comprise an apparatus as in any of the preceding examples adapted to deliver electrical stimulus directed to the retina of a patient having macular degeneration to arrest or reverse progress of the macular degeneration. Additionally or alternatively, a system may comprise an apparatus as in any of the preceding examples adapted to deliver electrical stimulus directed to the retina of a patient having retinitis pigmentosa to arrest or reverse progress of the retinitis pigmentosa. Additionally or alternatively, a system may comprise an apparatus as in any of the preceding examples adapted to deliver electrical stimulus directed to the retina of a patient having diabetic retinopathy to arrest or reverse progress of the diabetic retinopathy.

In another non-limiting example is a method of delivering stimulus to the eye of a patient comprising: delivering an electrical output using a first electrode disposed near the eye of the patient and a return electrode using a first current level; measuring a voltage between the first electrode and the return electrode and determining impedance between the first electrode and the return electrode; measuring an electrical field during the delivery of the electrical output using the first current level by a second electrode; and determining characteristics of electrode-tissue contact for each of the first and second electrodes using the measured field and determined impedance. Additionally or alternatively the method may further comprise using the determined characteristics to decide whether to: deliver electrical stimulus to the patient using at least one of the first and second electrodes with the return electrode; or issue an alert to a patient indicating that at least one of the first, second and return electrodes is inadequately coupled to tissue.

In another non-limiting example is a method of treating a patient with at least a first electrode and a return electrode, the method comprising: delivering a first stimulus targeting a deep portion of the eye including at least one of the optic nerve and the retina, the first stimulus comprising output pulses separated by inactive time periods; and during inactive time periods of the first stimulus, delivering a second stimulus targeting a different patient anatomy. Additionally or alternatively, the second stimulus is configured for stimulating tear production.

Another non-limiting example takes the form of a method of treating a patient with at least a first electrode and a return electrode, the method comprising: delivering a first stimulus targeting a deep portion of the eye including at least one of the optic nerve and the retina, the first stimulus comprising output pulses separated by inactive time periods; and delivering a second stimulus overlapping the first stimulus.

Additionally or alternatively, the first electrode is part of an eyepatch, the eyepatch also including a heating element, wherein the second stimulus is a warming stimulus configured to stimulate tear production. Additionally or alternatively, the first electrode is part of an eyepatch that also includes an optical output element, and the second stimulus is an optical stimulus delivered to the eye of the patient.

Another non-limiting example takes the form of a method of treating a patient comprising delivering an electrical stimulus to the patient's eye, sensing an electrical signal emanating from the patient's eye during a time period overlapping the electrical stimulus; determining whether the patient is experiencing phosphenes from the sensed signal and, if so, reducing an amplitude, duty cycle, or power level of the electrical stimulus or, if not increasing the amplitude, duty cycle, or power level of the electrical stimulus.

Another non-limiting example takes the form of a system for delivering stimulus to a patient comprising: a U-shaped pulse generator having a return electrode associated therewith; and a delivery apparatus to be worn on the head of a patient and having at least one stimulus delivery electrode thereon.

Another illustrative, non-limiting example takes the form of a system for delivering stimulus to a patient comprising: a pulse generator having a U-shaped housing adapted and configured to be worn on the neck of a patient, having therein operational circuitry including at least output circuitry configured to generate output electrical pulses; a plurality of stimulus delivery electrodes electrically coupled to the pulse generator and adapted, when worn by a patient, to deliver stimulus generated using the output circuitry to at least one eye of the patient. Additionally or alternatively the system further comprises at least one return electrode adapted for use as a return or indifferent electrode when output electrical pulses are generated. Additionally or alternatively, the at least one return electrode is disposed on the U-shaped housing. Additionally or alternatively, the stimulus delivery electrodes may be disposed on wires retractable into and extensible from the U-shaped housing. Additionally or alternatively the stimulus delivery electrodes may be disposed on a frame that is wearable by the user on the user's head. Additionally or alternatively the stimulus delivery electrodes may be disposed on a headband that is wearable by the user on the users head. Additionally or alternatively, the stimulus delivery electrodes may be disposed on a goggle adapted to fit over and about the eye of a user. Additionally or alternatively the pulse generator includes one or more ports for receiving a coupler that electrically couples to the stimulus delivery electrodes, allowing disconnection and reconnection thereof. Additionally or alternatively the pulse generator operational circuitry comprises a microcontroller associated with a memory having thereon instructions for generating therapeutic outputs, the microcontroller configured to control the output circuitry, and a power supply in the form of a replaceable battery. Additionally or alternatively the pulse generator operational circuitry comprises a microcontroller associated with a memory having thereon instructions for generating therapeutic outputs, the microcontroller configured to control the output circuitry, and a power supply in the form of a rechargeable battery.

Another illustrative and non-limiting example takes the form of a patient interface apparatus for delivery of stimulus to a portion of the head of a patient, the patient interface apparatus comprising: a first eyepiece adapted to fit about at least one eye of the patient; a frame or a strap to hold the first eyepiece on the head of the patient; wherein the first eyepiece comprises at least first and second electrodes electrically isolated from one another, the first eyepiece further comprising at least first and second electrical connectors separately coupled to the first and second electrodes. Additionally or alternatively the patient interface apparatus further comprises a pulse generator carried on the frame or strap and coupled to at least the first and second electrodes to issue therapy pulses therefrom. Additionally or alternatively the first eyepiece is configured to hold the first electrode on the patient's eyelid. Additionally or alternatively the first eyepiece is a closed eyepiece having a transparent portion through which the patient can see while wearing the first eyepiece. Additionally or alternatively the first eyepiece is a closed eyepiece having an opaque portion which the patient can see while wearing the first eyepiece, the opaque portion comprising a screen configured to display graphics usable to test patient visual acuity or performance.

Another illustrative and non-limiting example takes the form of a method of treating a patient having an eye disease comprising: a patient donning a neck-worn pulse generator containing operational circuitry including output circuitry configured to generate output electrical pulses; a patient donning a plurality of stimulus delivery electrodes electrically coupled to the pulse generator and adapted, when worn by a patient, to deliver stimulus generated using the output circuitry to at least one eye of the patient; the patient activating the pulse generator to deliver a stimulus to the eye of the patient; and the pulse generator issuing stimulus to the eye. Additionally or alternatively, the method further comprises, in response to the patient activation, the pulse generator testing impedance between one or more pairs of stimulus delivery electrodes to confirm appropriate contact with patient tissue and, in response to confirming appropriate contact with patient tissue, the pulse generator issues the stimulus to the eye. Additionally or alternatively the pulse generator comprises at least one return electrode thereon for use as a return or indifferent electrode when output electrical pulses are generated, and the step of the pulse generator issuing stimulus to the eye comprises using the at least one electrode on the pulse generator as a return or indifferent electrode. Additionally or alternatively the pulse generator comprises a U-shaped housing adapted to receive at least one extensible and retractable wire carrying at least one of the stimulus delivery electrodes thereon, such that the step of the patient donning the stimulus delivery electrodes comprises extending the wire from the pulse generator. Additionally or alternatively the stimulus delivery electrodes are disposed on a frame that is wearable by the user on the user's head, and the step of the patient donning the stimulus delivery electrodes comprises the patient putting on the frame.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE FIGURES

The drawings illustrate generally, by way of example, but not limitation, various embodiments discussed in the present document, and are not necessarily drawn to scale.

DETAILED DESCRIPTION

Figure 1:
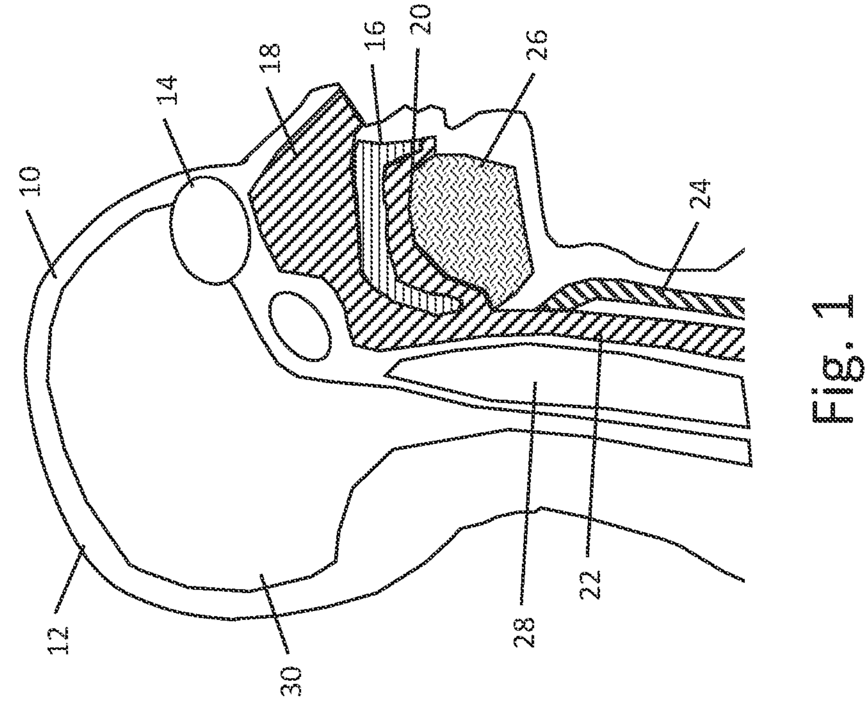
FIG. 1 shows a human head in a simplified form.

The present invention is generally directed to systems for delivering stimulus to the eye of a patient having a disease of the eye. In various examples, the condition to be treated may include one or more of the following: macular degeneration, inherited retinal disease, presbyopia, diabetic retinopathy, and glaucoma. In further embodiments, the condition to be treated may include one or more of the following: retinitis pigmentosa, Stargardt's, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia, gyrate atrophy, central retinal artery occlusion, central retinal vein occlusion, branch retinal artery occlusion, branch retinal vein occlusion, central serous chorioretinopathy, cystoid macular edema, ocular histoplasmosis, ocular toxoplasmosis, retinopathy of prematurity, amblyopia, strabismus, nystagmus, cataracts, refractive errors, and/or corneal conditions including corneal lesions and abrasions including surgical wounds, as well as dry eye, conditions amenable to nerve stimulation including by stimulation of the facial nerve, and any other ophthalmic, eye, or vision-related condition, disease, disorder, abnormality or damage. In alternative embodiments the systems disclosed herein can be used to optimize or improve vision for eyes that are "normal" or have no pathology.

In some examples, new systems and methods for delivering ocular modulation therapy are disclosed. As used herein, ocular modulation refers to the treatment of the eye with a signal, delivered non-invasively, or minimally-invasively, to achieve a therapeutic benefit. Therapeutic benefit may include, for example and without limitation, improving or altering blood flow, upregulating or downregulating synthesis, degradation, binding, release or activity of proteins, enzymes, DNA, RNA, polysaccharides or other endogenous physiological or pathological biomolecules; and/or upregulating, downregulating, activating, deactivating physiological or pathological biopathways, etc. Ocular modulation may be combined with the administration of pharmaceuticals, exogenously derived biomolecules, cell therapy, or photo-, electro- or magneto-reactive or active particles, such as nanoparticles, before, during or after an electrical signal is applied.

In some examples, the devices and systems disclosed herein are suited for use in conjunction with exogenous and/or endogenous stem cell transplantation therapies. For example, a method may comprise delivery of electrical stimulation before, during, or after stem cell transplantation to improve cell survival, repair and/or replacement. In some illustrations, the use of methods and systems disclosed herein may enhance native cell survival, transplanted cell survival, transplanted cell integration, and functional synapse formation and/or axon regeneration. Non-limiting examples of endogenous stem cell types which may be suitable for transplantation in combination with systems or devices of the present invention include Müller cells, retinal pigment epithelial cells (RPE cells) and ciliary pigmented epithelial cells (CPE). Non-limiting examples of exogenous stem cells suitable for transplantation according to some embodiments of the invention include neural stem cells (NSCs), mesenchymal stem cells (MSCs) derived from bone marrow, adipose tissue or dental pulp and stem cells from the inner cell mass of the blastocyst and induced pluripotent stem cells (iPSCs). See, for example, "Using Electrical Stimulation to Enhance the Efficacy of Cell Transplantation Therapies for Neurodegenerative Retinal Diseases: Concepts, Challenges, and Future Perspectives", Abby Leigh Manthey, et al., Cell Transplantation, Vol. 26, pp. 949-965, 2017.

In some examples, combination of therapy systems of the invention with biological or pharmaceutical agents may provide improved efficacy or reduced side effects associated with such biological or pharmaceutical agents when administered alone. Pharmaceutical agents currently used to reduce the growth of new blood vessels in wet AMD include anti-angiogenics such Bevacizumab (Avastin®), Ranibizumab (Lucentis®) and Aflibercept (Eylea®), etc. While the benefit of these agents for mitigating symptoms associated with wet AMD are known, these also may have side effects including increased eye pressure, inflammation of the eye and others. A benefit of systems disclosed herein includes modulation of cytokines and other endogenous inflammatory factors involved in the inflammation process. In some embodiments it is foreseen that administration of anti-angiogenic agents or other pharmaceuticals in combination with electrical therapy applied simultaneously with, before (e.g. 1, 2, 12, 24, 36, 48 and/or 96 or more hours before), or after (e.g. 1, 2, 12, 24, 36, 48 and/or 96 or more hours after), injection of such anti-angiogenics, at stimulation parameters used herein, may beneficially improve the efficacy and/or reduce the likelihood of side effects associated with administration of such agents.

Several different modes of energy delivery are disclosed, including mechanical (such as sonic energy, including for example, ultrasound), light-based (such as by the delivery of collimated or non-collimated light using, for example, a laser, a light emitting diode, etc.), electrical (such as by the delivery of an electrical signal), and/or magnetic (such as by generating a magnetic field or fields), and combinations thereof. In some examples, one mode of therapy delivery is used, while the same or a different mode of sensing is used to monitor therapy delivery. One component of several examples is the use of configurations that are adapted to provide enhanced tissue contact, enhanced therapy delivery location, improved efficiency of energy delivery, targeted therapy, reduced likelihood of tissue injury or irritation, and/or improved patient comfort and/or compliance.

FIG. 1 shows, in schematic form, a parasagittal section of a patient's head. The patient 10 has a skull 12 with the eye shown at 14. The hard and soft palate is shown at 16, separating the sinus cavity 18 and oral cavity 20, which meet behind the palate 16 and link to the esophagus 22 and trachea 24. The tongue is represented at 26. The upper end of the spinal column is also represented at 28. Collectively the air, bony structures and cartilage in this lower anterior portion of the head represents a relatively higher impedance than the brain 30, which extends in the posterior portion to the spinal cord. The brain and cerebrospinal fluid (CSF) that are present in this region are generally of lower impedance. The blood vessels throughout the brain are also relatively lower impedance.

For purposes of delivering electrical stimulus to the eye, an understanding of impedance in the general area is helpful. Gall et al. (2016) *Alternating Current Stimulation for Vision Restoration after Optic Nerve Damage: A Randomized Clinical Trial*, PLoS ONE 11(6): e0156134, using a finite element model, concluded that delivery of a current using transorbital electrodes and a return electrode on the right arm would result in the current flowing through the eyes and then through the brain stem and into the CSF at the base of the skull to thereby leave the head. For such a configuration, the authors determined that current tends to flow to and through the brain and then down through the CSF toward the return electrode, and may not substantially pass through the region of the air cavities 18, 20, 22 and 24 and surrounding tissue thereof.

Bone is a poor conductor, so optimizing electrode configurations requires consideration of how current, having passed through the eyes, can exit without creating unwanted stimulus to other structures such as in the ear and the vagus nerve, for example. On the other hand, a balance is needed to consider where to place the return electrode in a manner most convenient for the patient. Non-electrical stimuli, such as light-based or mechanical, need not complete a circuit, and can be directed toward the target tissue without necessarily considering where the energy will then flow, as the anticipated power levels for such modalities are unlikely to create side effects beyond the eye structure itself, as both light and mechanical energy would likely be attenuated by the eye and the surrounding bony structures that separate the eye from the brain itself.

Figure 2:
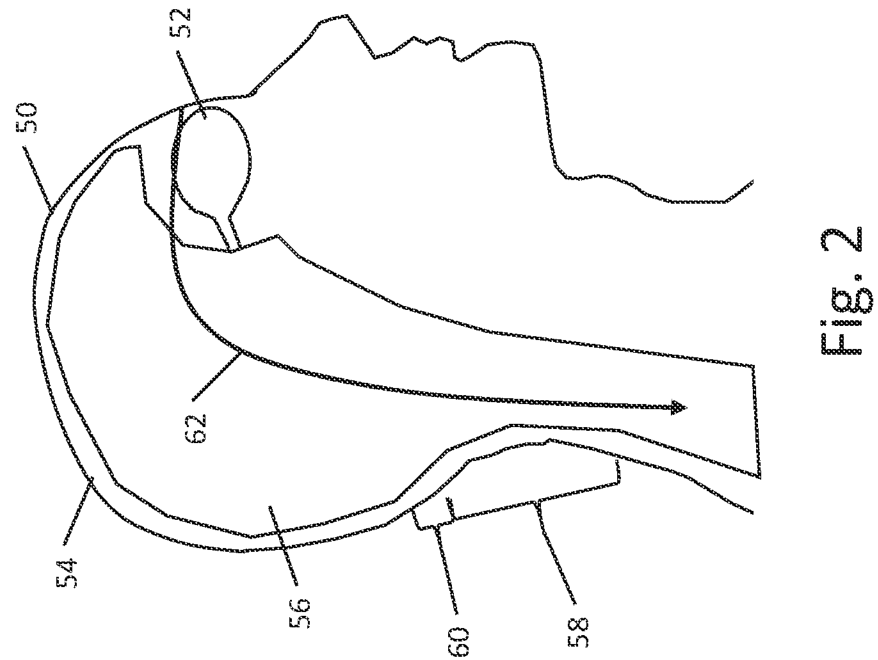
FIG. 2 illustrates the flow of current when applied in the vicinity of the eye.
Figure 3:
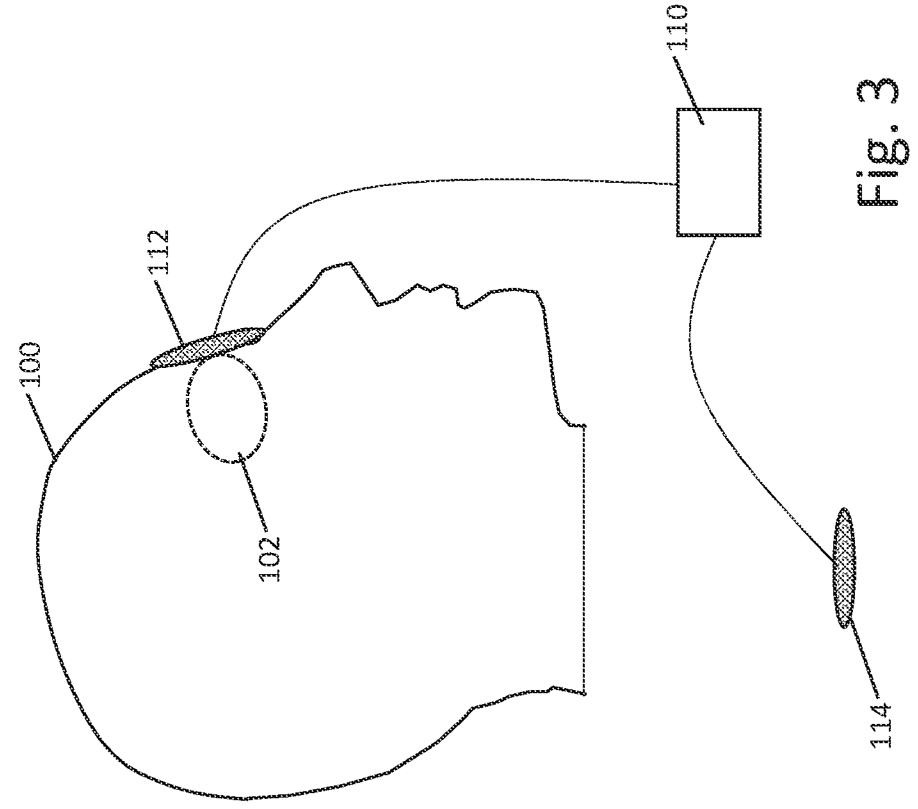
FIGS. 3-4, 5A, 5B, and 6-9 show several examples of stimulus application systems and devices.

FIG. 2 is a simplified model highlighting current conduction in the human head 50 when a current is applied to the eye 52 with a return electrode in the neck or below. In the example, the skull 54 serves to limit current flow and contains current within the brain 56 and associated fluid including the CSF and blood. A return electrode may be placed on the torso or limbs of the patient, and may also be placed on the neck, particularly in the region shown at 58, inferior to the lower margin of the skull shown at 60, as the anterior structures discussed with reference to FIG. 1 force current to flow more deeply into the middle portion of the skull, while the skull itself then directs current down generally through the brain stem and surrounding CSF as well as within the various blood vessels that also pass through the region highlighted by line and arrow 62. A return electrode may be placed more inferiorly than region 58, as desired. FIG. 3 shows an illustrative stimulus apparatus for delivery of stimulation to the eye. A patient 100 is shown, having eye 102. A pulse generator is shown at 110, with a stimulation delivery patch 112 on the eye of the patient, and a return electrode shown at 114. The return electrode 114 may be placed on a limb, such as on the right or left hand, or on the chest or shoulder of the patient. The electrodes may be TENS-type patch electrodes having a flexible patch of material with semi-adhesive gel on one side to hold the electrode in place and obtain good tissue contact for current delivery purposes. A similar system, but having two eye-patch electrodes 112, and two return electrodes 114, can be seen with the ScyFIX product described in U.S. Pat. No. 7,251,528 to Harold, the disclosure of which is incorporated herein by reference.

Figure 4:
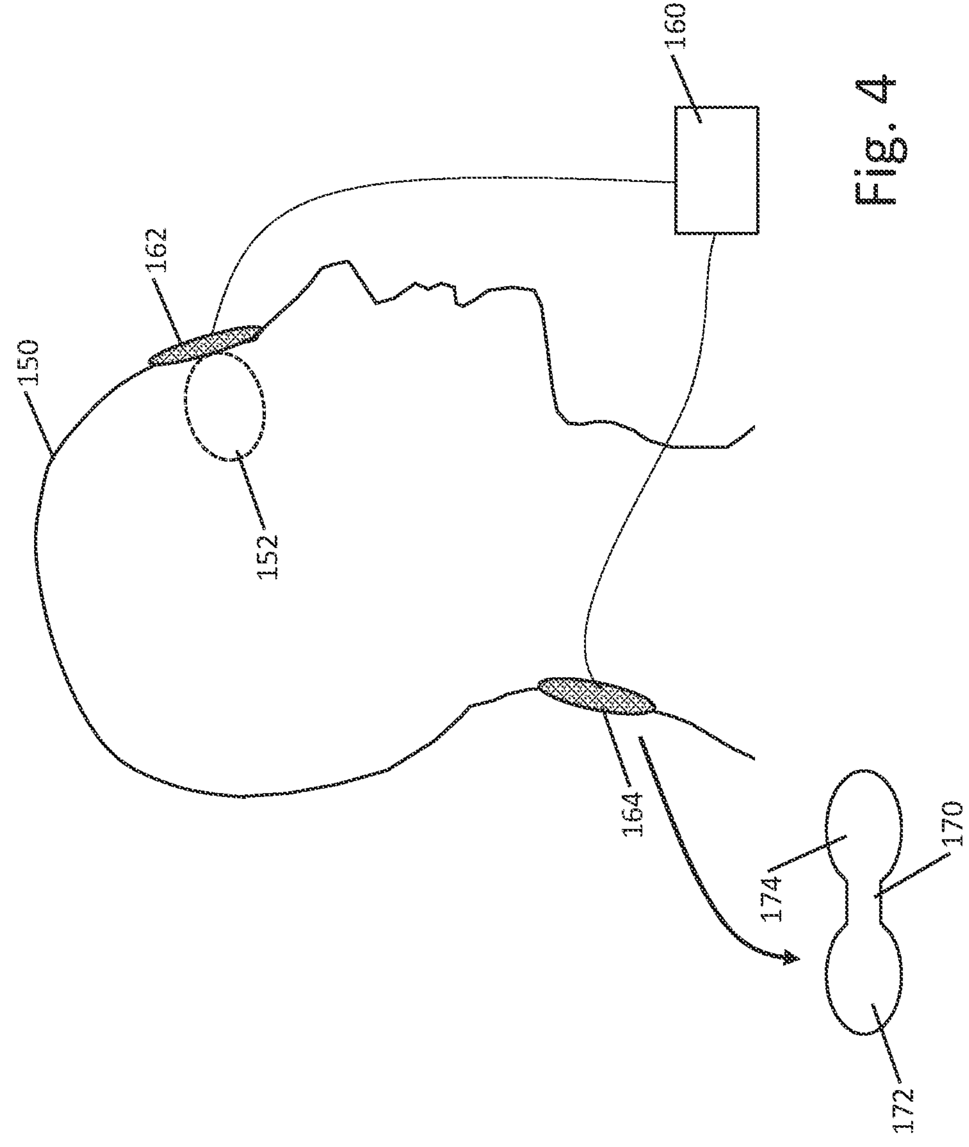

FIG. 4 shows another example. A patient 150 has a patch electrode 162 applied to one eye 152. The patch electrode 162 is coupled to a pulse generator 160, with a return electrode 164 placed on the neck of the patient, below the inferior margin of the skull. The return electrode 164 may be a simple patch, such as a circular or rectangular patch, or may have a particular shape such as that shown at 170, with a center portion of lesser width and two edge regions that are of larger area, as shown at 172 and 174; such a shape may be similar to a butterfly bandage, for example, with the electrically conductive portion thereof limited to regions 172, 174 to avoid focusing the return current over the spine, where the bony structures of the spine itself may increase impedance and the neural tissue of the spinal cord itself presents at least some risk of side effects if neural tissue is stimulated.

Figure 5A:
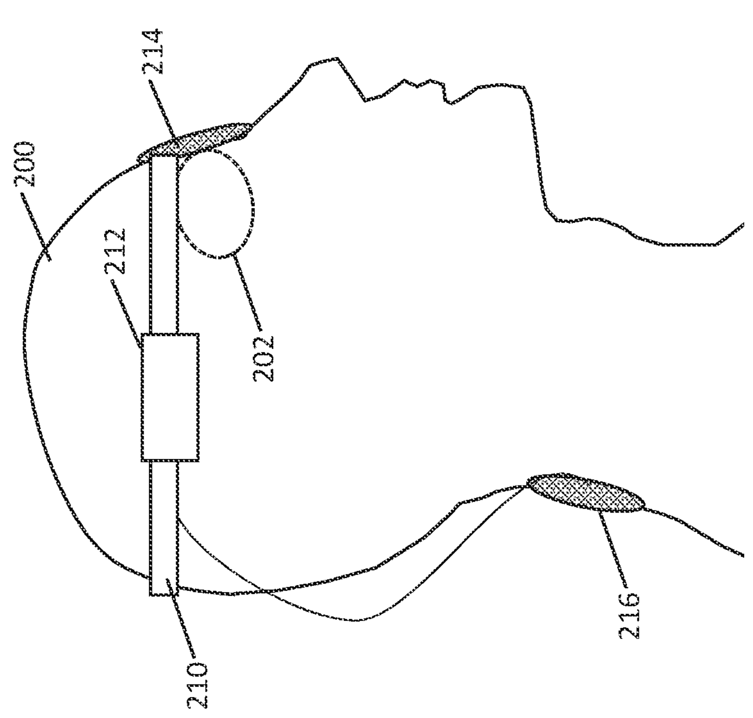

In some examples, the pulse generator 160 may be provided as a table-top piece that couples via cords to the electrodes 162, 164. In other examples, the pulse generator 160 may be a wearable element, such as by having a clip that allows the pulse generator to be attached to the belt of a user or onto an armband or a torso-worn harness. FIG. 5A shows another example. Here, the patient 200 is receiving stimulation on the eye 202 while wearing a headband 210 that carries a pulse generator module 212, with the headband integrating connections (which may be electrical, pneumatic, and/or optical, as desired and as further discussed in examples below) to an eye piece 214 and also a coupling via a tether to a return electrode 216. The headband 210 may be sized and fitted to the patient or may be elastic to conform to various head sizes, as desired. Wider, thinner, higher and lower headbands, or an entire cap, may be provided, if desired.

Figure 5B:
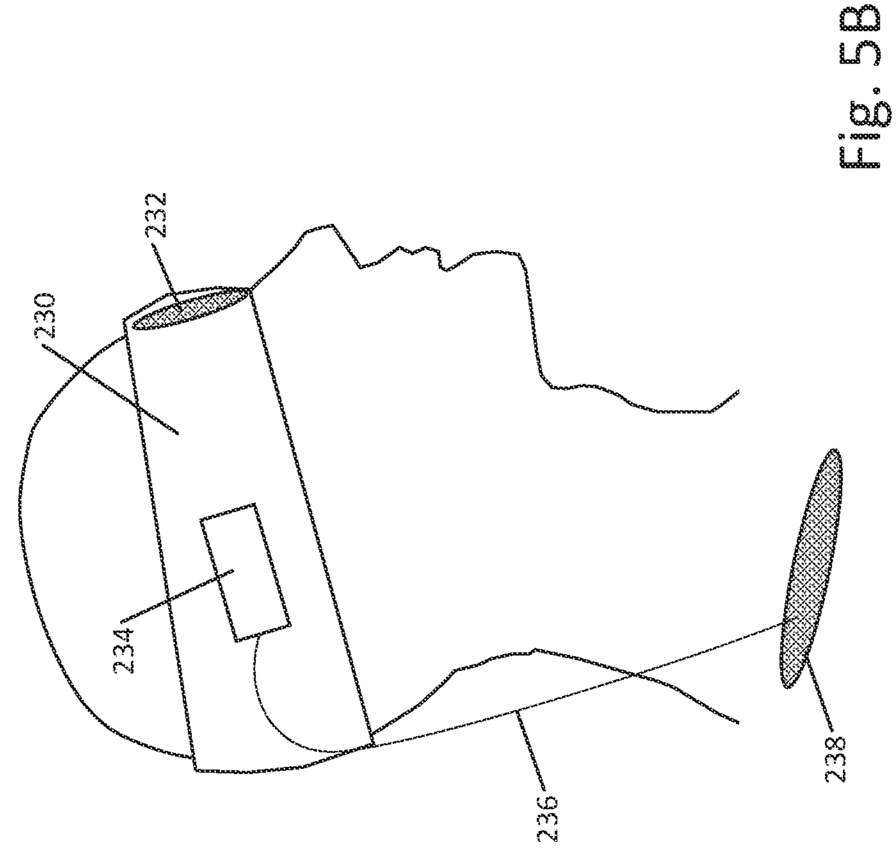

FIG. 5B shows yet another example. Here, the patient is shown wearing a larger headband 230, sized to cover the eyes and eyepiece 232. The headband carries the components of the stimulation pulse generator as indicated at 234. A return electrode 238 on a cord 236 can be placed elsewhere on the patient's body. In this example, the headband 230 may provide force to hold the eyepad on the patient's face with a more uniform force than the example of FIG. 5A. On the other hand, the example of FIG. 5A may be seen as less obtrusive to the patient; in short, there may be advantage and disadvantages to various different approaches.

Figure 6:
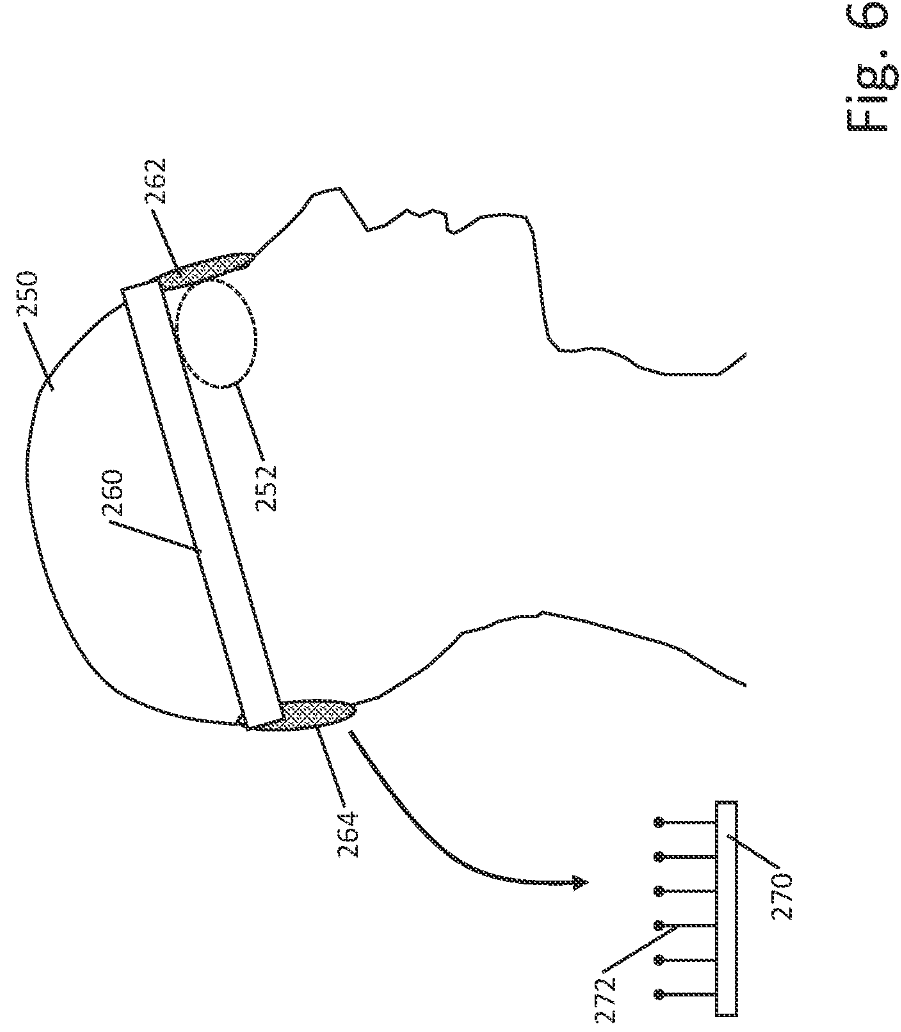

FIG. 6 shows another example. The patient 250 is receiving stimulation on the eye 252. A headband 260 carries the components of a pulse generator and couples to an eye piece 262 and return electrode 264. The headband 260 is not shown in this example as having a discrete housing such as shown above in FIG. 5 and instead carries the components including a battery and control circuitry in the band itself; a flex circuit may be used to provide comfort along with one or more small, replaceable or rechargeable batteries. In this example, no tether is needed for the return electrode 264 which is simply held against the back of the head. Electrode position in this example may not be electrically optimal, but the physical structure may be more convenient than having a separate tether. Attaining electrical contact to the back of the scalp may require the use of a conductive gel or the use of a return electrode having a base 270 and a plurality of elongated contacts 272 adapted to pass through the hair of the patient and press directly against the scalp.

Figure 7:
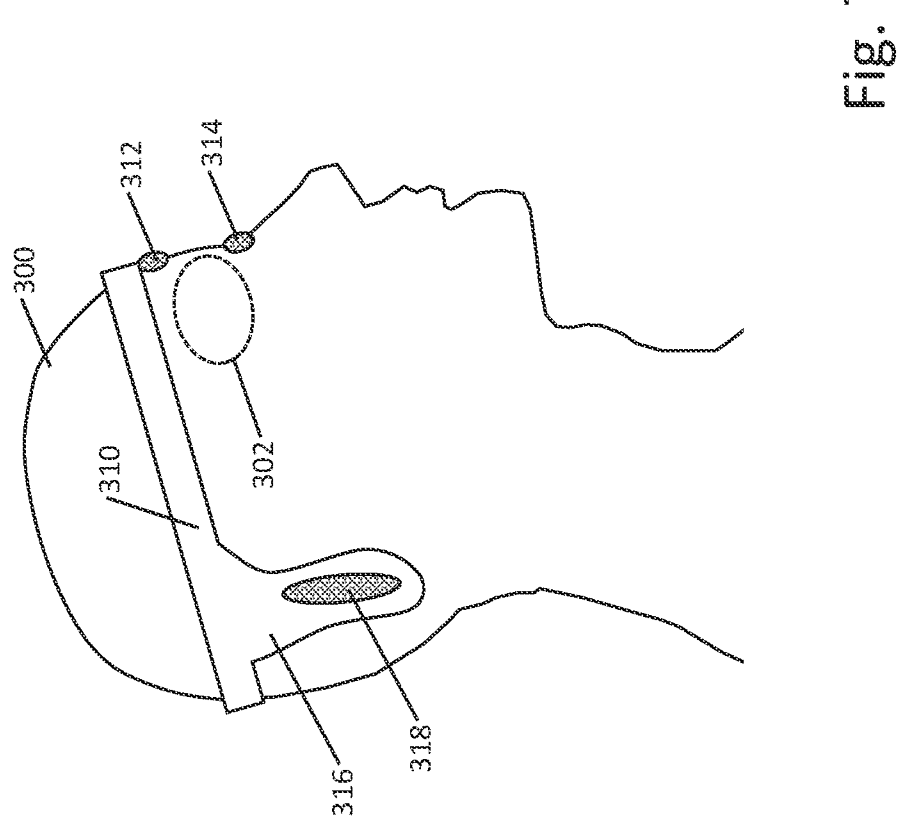

FIG. 7 shows another example. The patient 300 is wearing a headband 310 carrying the components of a pulse generator therein or thereon. A compound eyepiece includes first portion 312 on the upper eyelid, or coupled over the eyebrow, for example, and second portion 314 on the lower eyelid. Alternatively, first portion 312 may be medial of the eye 302 and second portion 314 may be lateral of the eye 302. Tethers or lead wires (not shown) may couple the portions 312, 314 to the headband. A return electrode 318 is carried on an earflap 316 shaped and designed to rest behind the ear and preferably somewhat behind and below the earlobe. Rather than an earflap 316, the return electrode 318 may be on a tether. While FIG. 7 only shows the right side of the patient, it should be understood that the eye piece 312, 314 and earflap 316 and return electrode 318 may be provided on the left side of the patient as well. In other examples, the compound eyepiece may have only an upper eyelid portion 312, or a lower eyelid portion 314.

For some examples, one or more pieces of the system may be replaceable without discarding the entire system. For example, a port for plugging in the return electrode 318, or eye piece 312, 314 may be provided so that the skin attaching electrodes can be replaced in the event of breakage, for example. In some examples, an adhesive patch is used, and the patch may be replaced when the adhesive ceases to work. In some examples, adhesive and conductive patches are applied over electrodes so that the patches can be replaced without requiring replacement of the electrodes.

Figure 8:
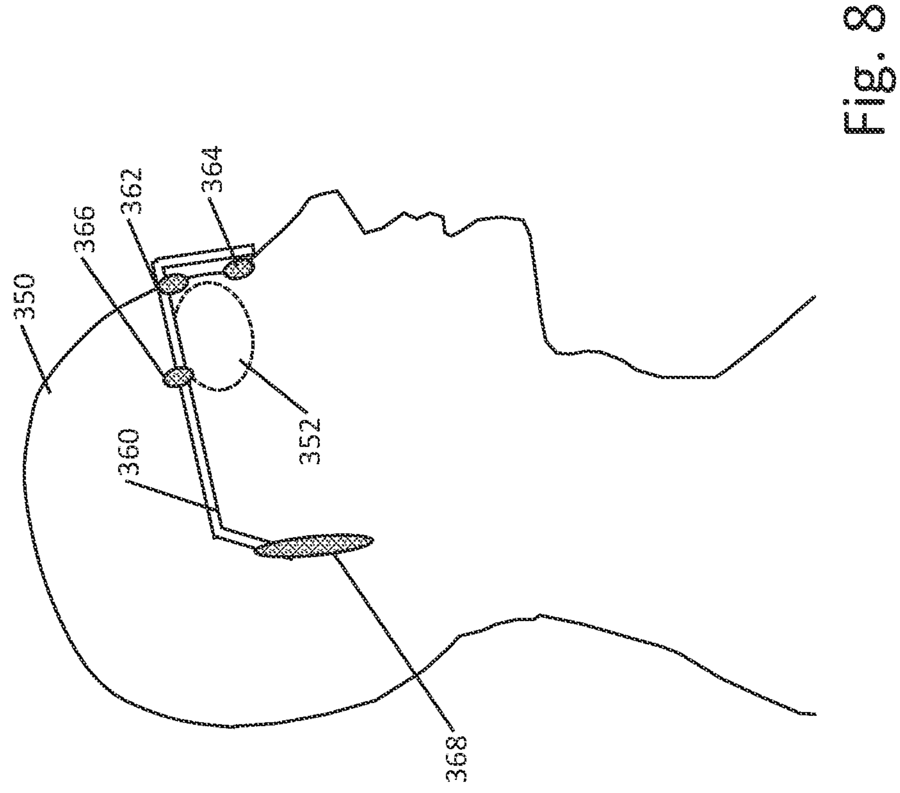

FIG. 8 shows another example. Here the patient 350 receives stimulus in the vicinity of the eye 352 by wearing a frame 360, similar to that for eyeglasses, which carries a plurality of electrodes. Not all of the electrodes are needed in some embodiments. The front portion of the frame 360 carries inferior electrode 364, superior electrode 362, and temporal electrode 366. For example, the weight of the frame itself may be used to hold electrodes 362 and 364 in place, while temporal electrode 366 is placed using an adhesive patch. The electrodes toward the front portion of the apparatus may be described as frontal electrodes, while the return electrode 368 is placed more rearward on the patient, such as behind the ear as shown or elsewhere such as on the back of the neck. The electrodes may also be associated with springs that press the electrodes into tissue contact. The return electrode 368 is placed toward the end of the earpiece of the frame 360. The frame 360 may integrate the electronics for controlling stimulation delivery and communicating with a separate device, such as a cellphone, tablet, or laptop, while also holding the batteries and wire connections to each electrode. If desired, the frame 360 may include a recharging port to allow rechargeable batteries to be replenished. In some examples, a rechargeable battery may be recharged using inductive recharging by providing an inductor and rectification circuit in the pulse generator and using a separate charger to generate magnetic fields that will stimulate the inductor to recharge the battery.

The inclusion of plural frontal electrodes may be useful in several distinct ways. For example, each electrode 362, 364, 366 may be separately addressable, to allow shaping of the stimulation field as it is delivered. In another example, one electrode may be the active electrode for stimulus delivery, while the other electrodes are used to monitor stimulation delivery to confirm, for example, that tissue contact is being achieved. In some examples, the plural frontal electrodes are used to test electrical contact in a first phase and, if electrical contact is good, stimulation can be delivered or, if electrical contact is not good, the patient may be prompted to modify positioning of one or more electrodes. In another example, electrode contact may be tested and only those electrodes showing acceptable contact are used in stimulation.

For example, a test current between two frontal electrodes may be generated, and the output can be measured by a third frontal electrode, while the voltage between the two active electrodes is measured. In this example, dividing the voltage between the two active electrodes by the test current would yield impedance for the active electrodes. Meanwhile monitoring of the voltage during test by the third frontal electrode may allow determination of electrical contact with the third electrode by comparing the voltage to a threshold. Thus, for example, test current could flow from electrode 364 to electrode 366 while voltage is measured with electrode 362, testing all three tissue contacts interfaces at once. Impedance may be monitored to ensure efficacy and/or safety, as well as patient status and physiological condition, as discussed as well in U.S. patent application Ser. No. 16/589,383, filed Oct. 1, 2019 and titled SYSTEMS AND METHODS FOR CONTROLLING ELECTRICAL MODULATION FOR VISION THERAPY, the disclosure of which is incorporated herein by reference.

In some embodiments therapy outputs are provided to cause firing of neurons within the eye, particularly in the retina. Such firing of the neural tissues occurs when an action potential threshold of a particular neuron is exceeded. In normally behaving cells, receipt of incident light causes neural firing in patterns that the visual system can interpret as an image. Sometimes firing occurs due to non-visual inputs. A phosphene may be understood as a ring or spot of light produced by pressure on the eyeball or direct stimulation of the visual system other than by light. Application of electrical signals to the region of the eye can produce phosphenes, when the electrical signals deliver enough energy to cause depolarization of neural cells. In several embodiments, the purpose of electrical stimulation is to affect neural tissue, and the presence of phosphenes can play a role in determining therapy efficacy. In some examples, phosphenes themselves are indications of therapy efficacy, and firing of neurons is a goal of therapy. In other examples, phosphenes provide a way of determining whether input electrical therapy is reaching desired target tissue. In still other examples, phosphenes may be used in a threshold setting manner, by delivering therapy to generate phosphenes, confirming that electrical pulses are reaching target tissue in the retina, for example, in the vicinity of the macula, and then setting one or more factors of the signal intensity (amplitude, pulse width, frequency) for therapy at, below, or above the determined phosphene threshold. Further examples for performing and using phosphene thresholds are disclosed in U.S. patent application Ser. No. 16/589,383, the disclosure of which is incorporated herein by reference.

Figure 9:
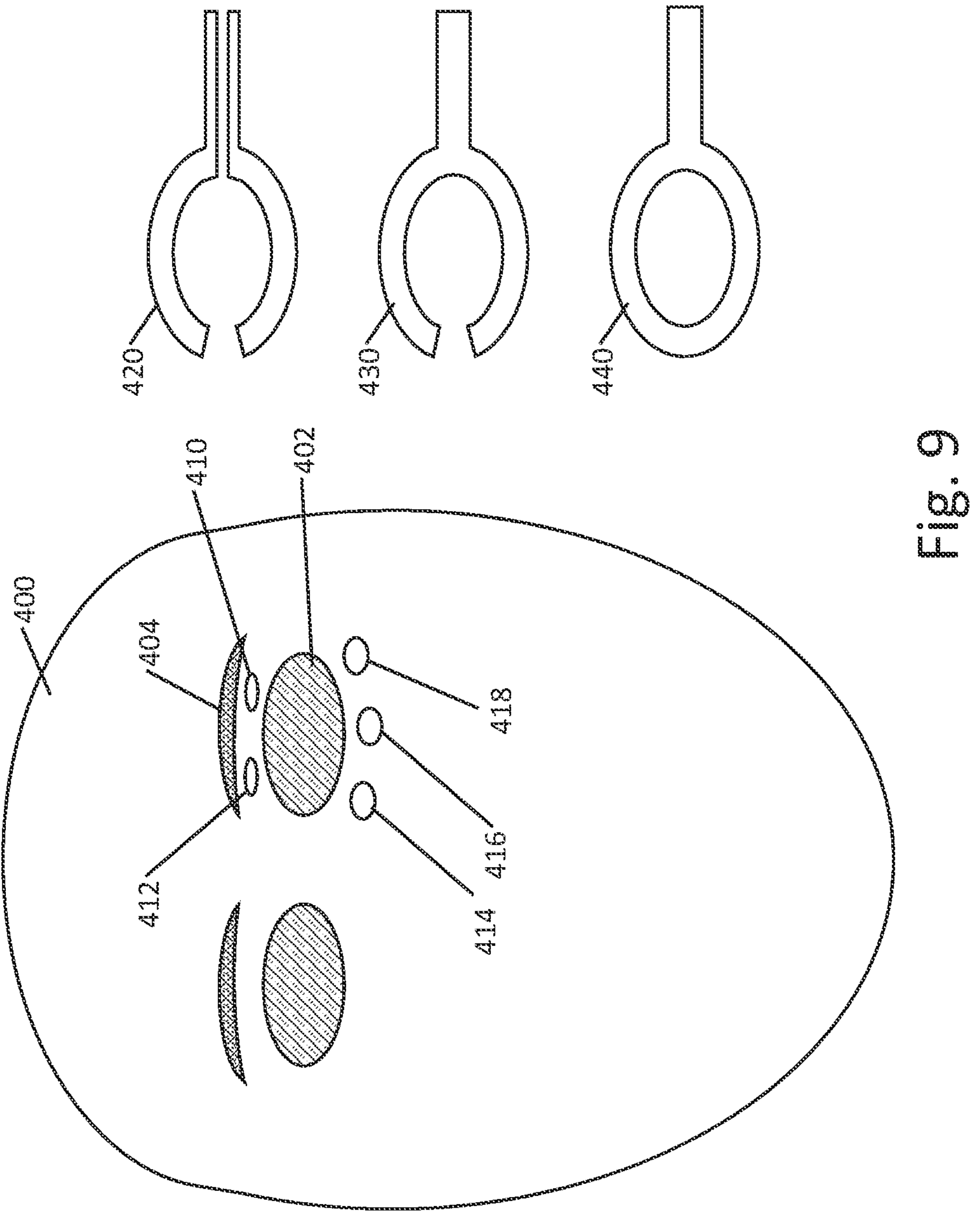

FIG. 9 shows another example, highlighting electrode position around the eye. The patient 400 is to receive stimulation on the eye 402. When looking to place the electrodes around the eye, avoiding the eyebrow 404 may be useful. Thus, here, two superior electrodes 410, 412 are shown on the upper eyelid, with three inferior electrodes at 414, 416, 418. In some examples, the superior electrodes 410, 412 may be provided on a strip of material, such as an adhesive strip, and may be connected to wires separate from one another so each may be separately addressed. The inferior electrodes 414, 416, 418 may likewise be provided on a strip of insulative or dielectric material and provided with individual wires to allow separate activation. The five electrodes shown may be on separate strips of material as shown at 420, or on a single, C-shaped-piece as shown at 430, or may be provided on a loop as shown at 440. Separate activation of one or more pairs of electrodes to test impedance between contact pairs, and/or measuring voltage with other, inactive electrodes, may be used to confirm adequate electrical contact as part of a therapeutic regimen. A return electrode may be provided as shown above in FIGS. 3-8.

More or fewer electrodes may be provided than that shown. In some examples there may be a single electrode over the eyes, or one electrode for each eye, or more than one electrode for each eye. In some examples, a plurality of electrodes on a single eye may serve different purposes at different times. For example, a set of several electrodes on one eye may be used to deliver ocular modulation therapy by making all the electrodes anodes or cathodes at once, such as by linking each electrode to a single output, or by linking individual electrodes to separate outputs with each output set as an anodic or cathodic output. The same set of several electrodes may be used for ocular modulation therapy, or, alternatively, a test output, by having one electrode serve as anode or cathode, relative to a far field return electrode, while other electrodes are used to monitor electrical fields in order to determine tissue contact characteristics. Assuming, for example, that ocular modulation therapy is delivered at a duty cycle, such as by delivering a constant current output pulse having a duration D, and then waiting a period of interpulse time, I, before a next output pulse, the interpulse period may be used to deliver a different therapy such as a therapy adapted to induce tears which would reduce local impedance. Some illustrative stimulation therapies for treatment of dry eye or tired eye, which may add to patient comfort and/or increase tear production, are disclosed in U.S. Pat. No. 9,687,652, titled STIMULATION PATTERNS FOR TREATING DRY EYE, the disclosure of which is incorporated herein by reference as illustrating such patterns. Some such patterns for inducing tears may use a range of, for example, 30 to 150 Hz frequency, and a current in the range of 100 microamps to 10 milliamps, with square, triangular or sinusoidal (or other shaped) waveform. This interpulse stimulation may be delivered using selected pairs of the electrodes that are located on/around the eye, and may omit the use of the distant return electrode, thus focusing the stimulation on the naso-lacrimal region, rather than directing current and electrical field deeper into the eye structure itself. It may be noted that such localized stimulation delivery may use a higher current, without increasing applied power or voltage, as stimulation is delivered between a far more closely spaced bipole (1-5 cm, for example) than when delivering the ocular modulation therapy to a return electrode that is 10 cm or more away from the delivery electrode (s).

In some approaches, a heating or warming apparatus is included in the eyepiece. A resistive or inductive heating element may be used, for example. Localized warming can improve electrode-skin interface characteristics by causing the patient to secrete sweat, tending to reduce local impedance and would aid in delivering stimulation that reaches the desired structures at reduced power levels. In addition, localized warming may loosen or relax the tear ducts and/or Meibomian glands, thereby encouraging tears to flow in the area.

In some examples, localized impedance is measured as stimulation is delivered over time—so, for example, in a therapy session having a duration (such as 5 minutes to 1 hour, or more or less), impedance may be measured at intervals such as every second, or every 10 seconds, or some other interval as desired. If tear inducing electrical or thermal stimulation, or sweat encouraging thermal effects are applied, as impedance drops over time it may be determined that the impedance characteristics have improved and the warming or tear-inducing electrical stimulation may be duty-cycled down or off, to avoid patient discomfort from excessive tears or sweat. For example, a threshold impedance may be established at the start of stimulation, and a change of greater than some percentage, such as a reduction by half of the localized sensed impedance, may trigger turning off or down-cycling elements of the stimulation. Secondary stimulation such as for glaucoma (which may again focus on thermal or electrical treatment to modulate, facilitate, unblock, or ease fluid flow), or for cosmetic purposes, may be delivered as well, if desired.

One or more inductive elements may be provided to deliver magnetic fields to the region of the eye as well, again using either inactive electrodes, taking advantage of the time between ocular modulation therapy pulses, or using an inductive element or the like which is not part of the ocular modulation therapy circuitry. Magnetic field therapy may thus also be provided.

Some examples may omit a separate return electrode, if desired. However, it is generally contemplated that ocular modulation therapy will often be provided using a return electrode placed elsewhere on the patient, to ensure that the electrical field is directed into structures deep in the eye, such as to the retina and macula. In an example, one eyepatch or goggle may be used as the active delivery electrode, while the other is a return electrodes. For example, if multiple electrodes are provided on each eyepatch, the electrodes on the "output" patch may be individually and/or separately activated from one another, while the electrodes on the other eyepatch may be coupled together in common as a larger return electrode. In another example, the "return" eyepatch may selectively have one or more electrodes that are located near midline (that is, closer to the other eye) inactivated to discourage current flow through superficial tissue.

Figure 10:
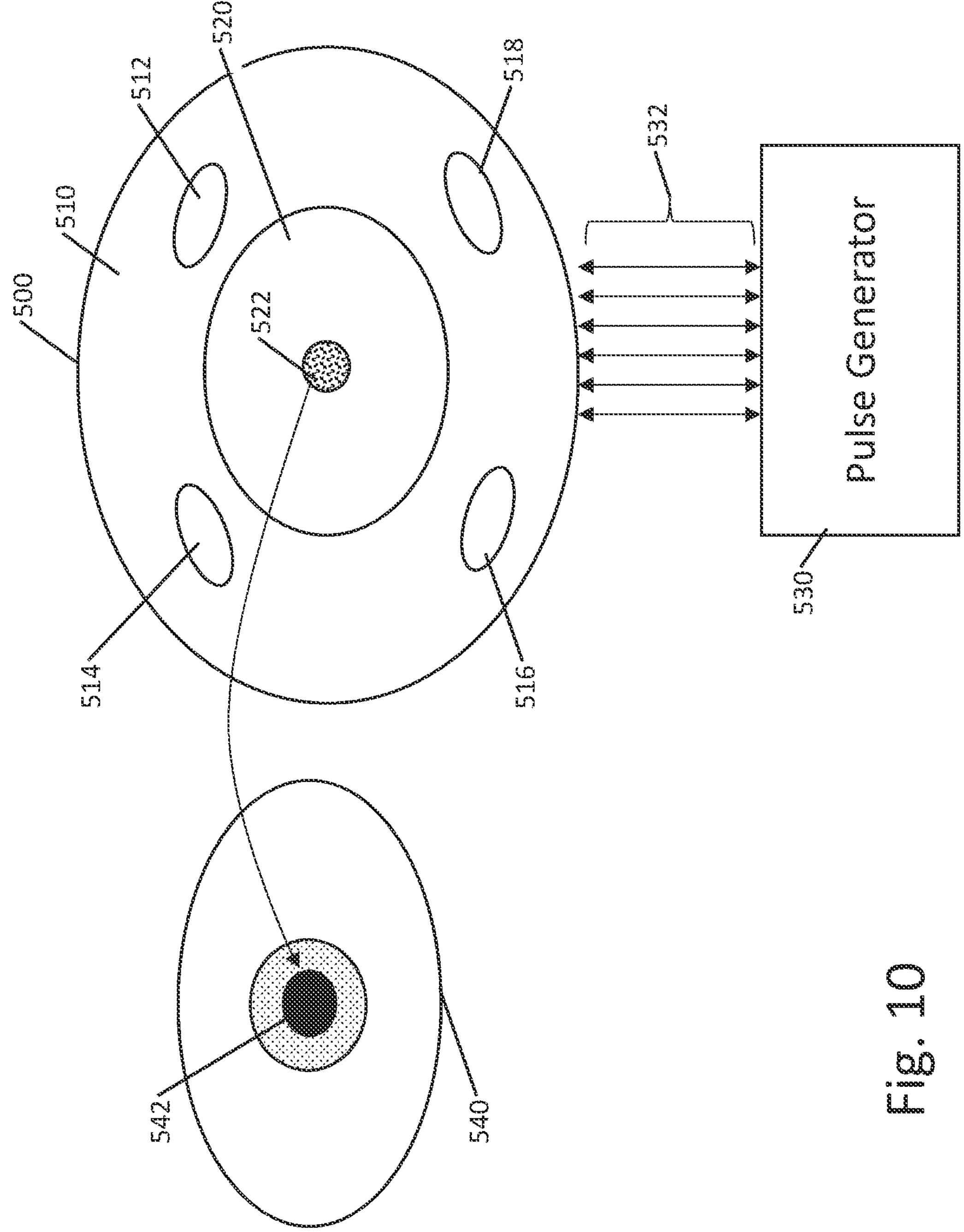
FIGS. 10-11 illustrate multi-electrode examples.

FIG. 10 shows another example. Here an eyepatch is provided as shown at 500, with a first, tissue contacting portion at 510 and a goggle portion at 520. A plurality of electrodes 512, 514, 516, 518 are provided on the tissue contacting portion 510. In some examples, the tissue contacting portion 510 is a soft or flexible material. In one example, the electrodes 512, 514, 516, 518 are provided on a flex circuit or are themselves flexible to allow easy movement relative to patient tissue. In another example, the electrodes 512, 514, 516, 518 may be in the form of metal beads or protrusions that extend from the face of the tissue contacting portion 510 to provide enhanced contact. The tissue contacting portion 510 may be sticky, if desired, to promote tissue contact and adhesion. In still another example, dry electrodes as described by Stauffer et al., *Skin Conformal Polymer Electrodes for Clinical ECG and EEG Recordings*, Adv. Healthcare Mater. 2018, 7, 1700994, may be incorporated including, for example, electrodes having soft polymers with mesh-metal structures, conductive fillers, nanotubes, nanowires, or microstructures thereon may be used.

The eyepatch 500 may be provided on a headband that holds it under mild pressure against the tissue surrounding the patient's eye. The goggle portion 520 may carry an optical element or elements as shown at 522. The optical element 522 may be, for example, a laser diode adapted to issue light into the eye of the patient for therapeutic or diagnostic purposes. The optical element 522 may include one or several light emitting elements and a camera, in some examples, to allow the eye to be illuminated as an image is captured using the camera. The camera may be used to capture an image of the patient's anatomy, such as to capture an image of the retina. Retinal images may be captured over time to monitor disease and/or therapy impact, for example, by comparing images to identify changes over time showing progress or reversal of disease impacts, for example as described in U.S. patent application Ser. No. 16/589,383, filed Oct. 1, 2019, the disclosure of which is incorporated herein by reference. The goggle portion 520 may be clear in some examples to allow the patient to engage in daily activities, such as light chores, exercise, reading or watching television during stimulation delivery.

The apparatus is powered by a pulse generator shown at 530. A plurality of connections 532 are provided to the eyepatch 500 to allow separate addressing of the various electrodes and other elements of the eyepatch, as needed. In some examples, shown below, the eyepatch may include an aperture coupled to a tube that provides negative pressure inside of the eyepatch, as further described below, and at least one of the connections 532 may be a hollow tube to allow suction to be applied. In some examples, tissue contacting portion 510 may comprise a balloon, such as a compliant balloon made of a polymeric material (or any other suitable material), which can be inflated by air, nitrogen, saline or other fluid, as desired, to achieve enhanced tissue contact. For such an example, at least one of the connections 532 may be adapted for delivery of the inflation medium. As an alternative, a piezo elected element may be provided to move the electrode into a desired contact position.

In one example, the goggle portion 510 may be electrochromatic. When a diagnostic test is not needed, the electrochromatic goggle portion can be generally clear, and when a diagnostic test is needed, the electrochromatic goggle portion can be transitioned to an opaque state to block ambient light while a diagnostic test, such as image capture of the retina, is performed. To transition the electrochromatic goggle, an electric or magnetic field is applied or modified using the pulse generator 530 as is known in the art. The opaque state may be useful to encourage dilation of the pupil for retinal image capture. The pulse generator 530 may provide an alert to the user before darkening the electrochromatic goggle portion.

In other examples, the goggle portion 520 may be configured with a screen, such as the type used in virtual reality goggles. The screen may be used in diagnostic tests. For example, with a camera included, placing a dot on the screen and having the patient track the dot with his eye may be useful to determine whether the patient appropriately tracks the target as it moves or when it is static. For example, with macular degeneration, the patient may not look directly at the target in order to see it, as the center of the field of vision may not work well for such a patient, thus, such tracking exercises provide a measure of the patient's disease state. Other diagnostic tests may include patient queries, rather than observations. Illustrative tests may include, for example, a Snellen test, a random E test, a kinetic field test, a Goldmann test, an Amsler test, a Humphrey test, or other tests for contrast, visual acuity, visual field, tracking, color, brightness, and/or peripheral field.

The overall structure is designed such that the tissue contacting portion 510 can be placed over and around the eye 540 of a patient, with the goggle portion 520 generally over the central portion of the eye and the pupil 542 in particular. While the optical element 522 is shown generally in the center of the goggle portion 520, it is also contemplated that a plurality of optical elements may be provided away from the center of the goggle portion 520, either with or without a centrally located element. For example, moving the optical element 522 away from the center of the goggle portion 520 may provide unobstructed vision to the patient during a therapy session. In an example, light emitting optical elements may be at the periphery of the goggle portion 520, with a camera located centrally. Alternatively, a single light emitting element may be in the center, while a plurality of camera elements are at the periphery. In another example, a plurality of cameras and light sources are located both centrally and at the periphery of the goggle portion. In still further examples, light and camera elements may be placed anywhere in the goggle portion 520.

Figure 11:
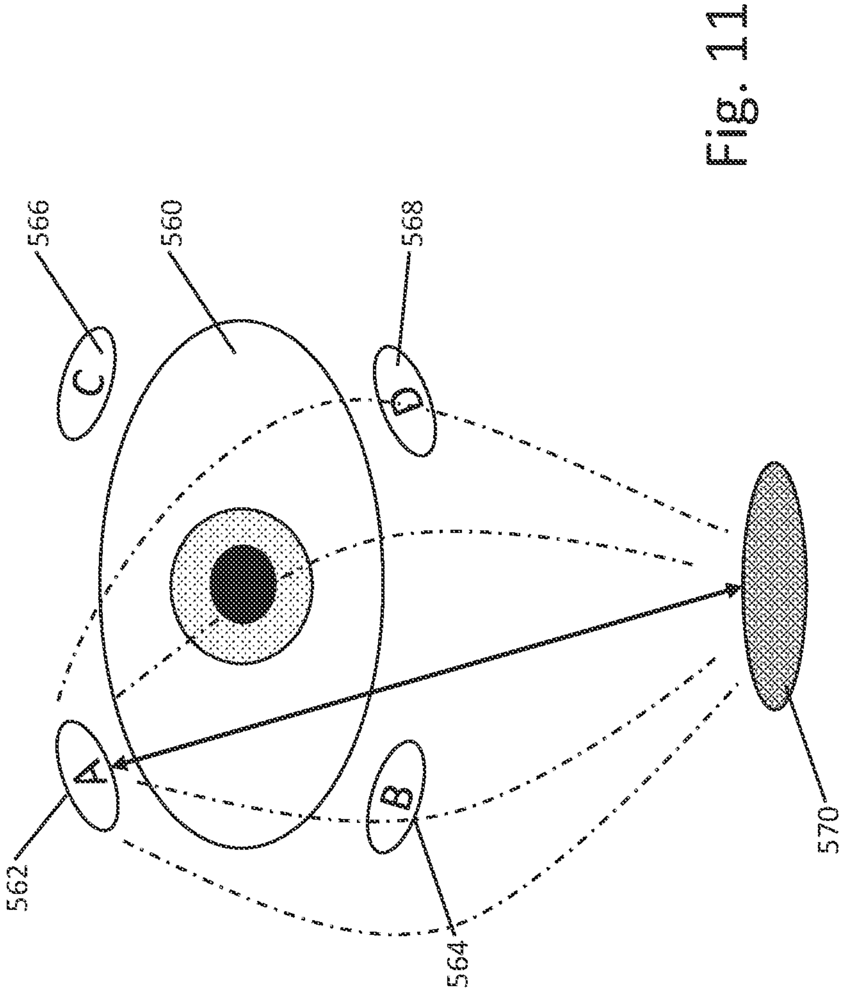

FIG. 11 illustrates various features of a multi-electrode system. The electrodes of a system are shown relative to an eye, without other structures of the system shown. Around the periphery of eye 560 are electrodes A 562, B 564, C 566, and D 568, with a return electrode 570 located elsewhere on the body. For therapy or test purposes a current may flow between electrode A 562 and the return electrode 570. During such current delivery, the voltage on the return electrode 570 may illustratively be treated as the ground or reference of the circuit, and voltages at electrodes A 562, B 564, C 566, and D 568 can be measured or sampled. The voltage measured at electrode A 562 can be used to determine the impedance between electrode A and the return electrode 570, indicative of both the bulk (body) impedance of the system and the tissue-electrode interfaces at electrode A 562 and return electrode 570, as well as impedance of the circuitry and connections linking the current delivery and/or voltage measurement circuitry to the electrode A 562 and return electrode 570. Meanwhile, the measurement of voltage at electrodes B 564, C 566 and D 568 provide information as to the quality of tissue-electrode interface for each respective electrode, as the issuance of current from electrode A will cause detectable electrical field (as indicated by the broken field lines shown) at each of the other electrodes in the vicinity of A. For example, through testing on a given patient or by use of modelling based on a patient population, a determination as to the expected "normal" sensed field at each of electrodes B 564, C 566 and D 568 for a given current level at electrode A can be established, either generically for any patient or on a patient-specific basis. When the sensed fields at electrodes B 564, C 566 and D 568 are within the expected range, it may be assumed that tissue-electrode contact is adequate and no faults exist for such electrodes.

In some examples, one electrode near the eye and a return electrode may be used to deliver the current used during such testing. In other examples, testing of tissue interface may be determined by duty cycling one electrode off while keeping other electrodes active. In other examples, rather than relying on field sensing, the impedance of each of the eye electrodes A 562, B 564, C 566 and D 568 may be directly measured using the return electrode 570 as ground. In still other examples, because the impedance from, say electrode A to electrode 570 may be relatively large due to the large amount of intervening tissue (skin, eye, nerve, brain, bone, etc.), a differential measurement may be made by determining sensed impedance for each of electrodes A 562, B 564, C 566 and D 568 relative to the return electrode 570 and comparing the results to one another. In still another example, a system may be adapted to confirm good tissue contact at the eye electrodes a 562, B 564, C 566 and D 568 using local testing, such as measuring the impedance from A 562 to B 564, then A 562 to C 566, etc. through all or a selected subset of all such combinations (A/B, A/C, A/D, B/C, B/D, C/D) to allow a system to inform the user as to where the problem lies if high impedance is detected—that is, whether the issue is at the eye electrodes A 562, B 564, C 566 and D 568, or with the return electrode 570. Thus, in a method, impedance during ocular modulation therapy may be monitored and, if out of bounds, the system may test the eye electrodes A 562, B 564, C 566 and D 568, to the exclusion of return electrode 570, in order to instruct the user on whether the high impedance is because of one or more eye electrodes being in poor contact with the skin, versus whether the return electrode has poor contact or positioning.

Figures 12A, 12B, 12C:
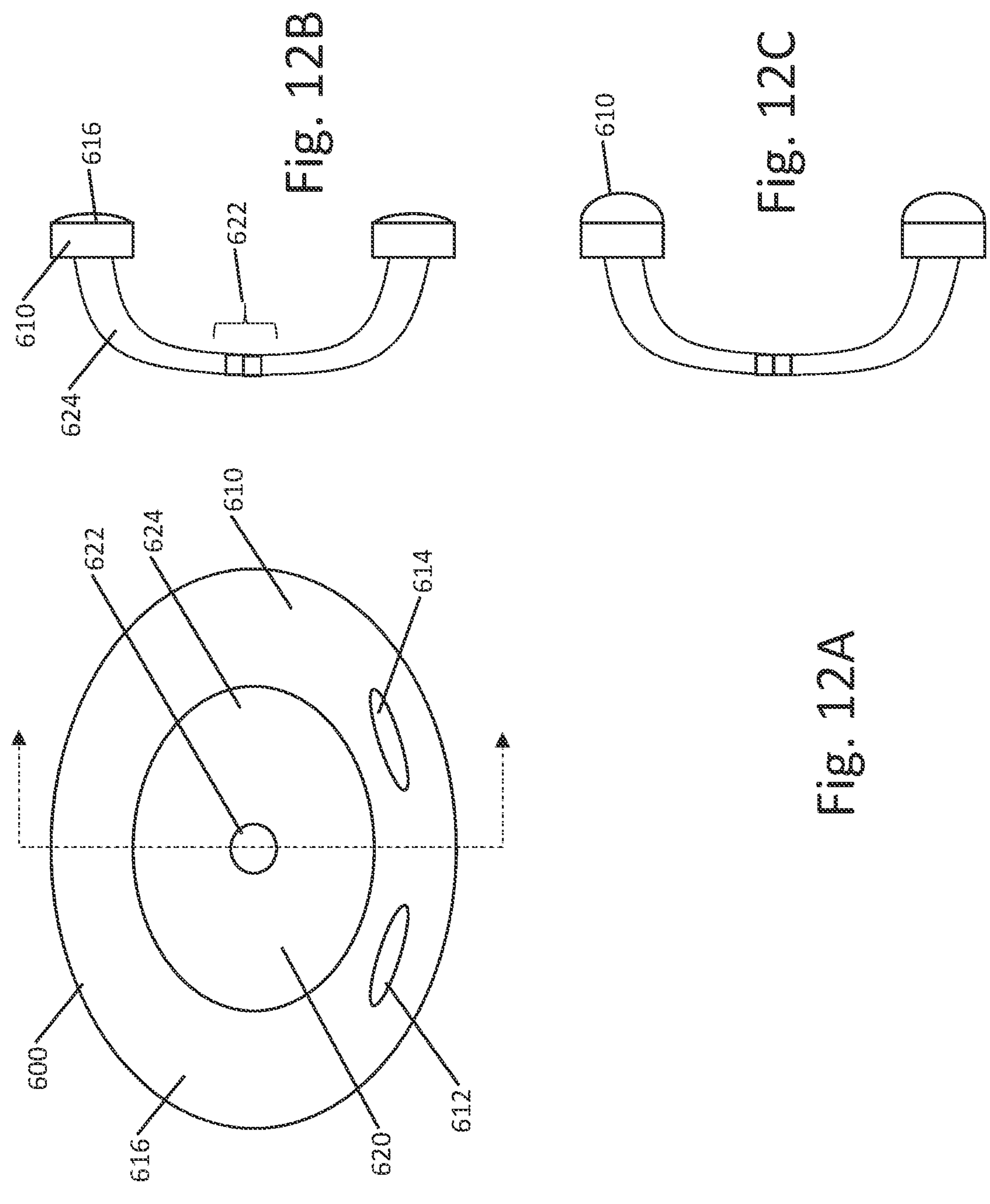
FIGS. 12A-12C, 13A-13B, 14-17, 18A-18B, 19, 20A-20D, and 21A-21C show additional illustrative stimulus application systems and devices.

FIG. 12A shows another example. Here, an eyepatch is provided as shown at 600 with a tissue contacting portion 610 having electrodes 612, 614 and contact portion 610, and a goggle portion at 620 having a window 624 and optical element 622. The window 624 may be clear, opaque, colored, or electrochromatic and the optical element 622 may include a camera and/or light emitting element, and plural such optical elements 622 at central, peripheral or other locations may be provided. The tissue interface 610 in this example may be provided with an inflatable member, as shown in the side section views at 12B and 12C, in which the tissue contacting portion 610 holds the inflatable element 616 which can be inflated as shown in FIG. 12C to enhance tissue contact. Such inflation may be used to create a seal, or to press the electrodes 612, 614 more firmly against the skin. Use of a compliant balloon (such as using a polyurethane or silicone material) may allow more complete tissue contact to be made than with a non-compliant (made using for example nylon or polyester) or foam structure. In other examples, a gel type structure, such as a polymeric gel contained within a polymeric skin, may be used.

Figures 13A, 13B:
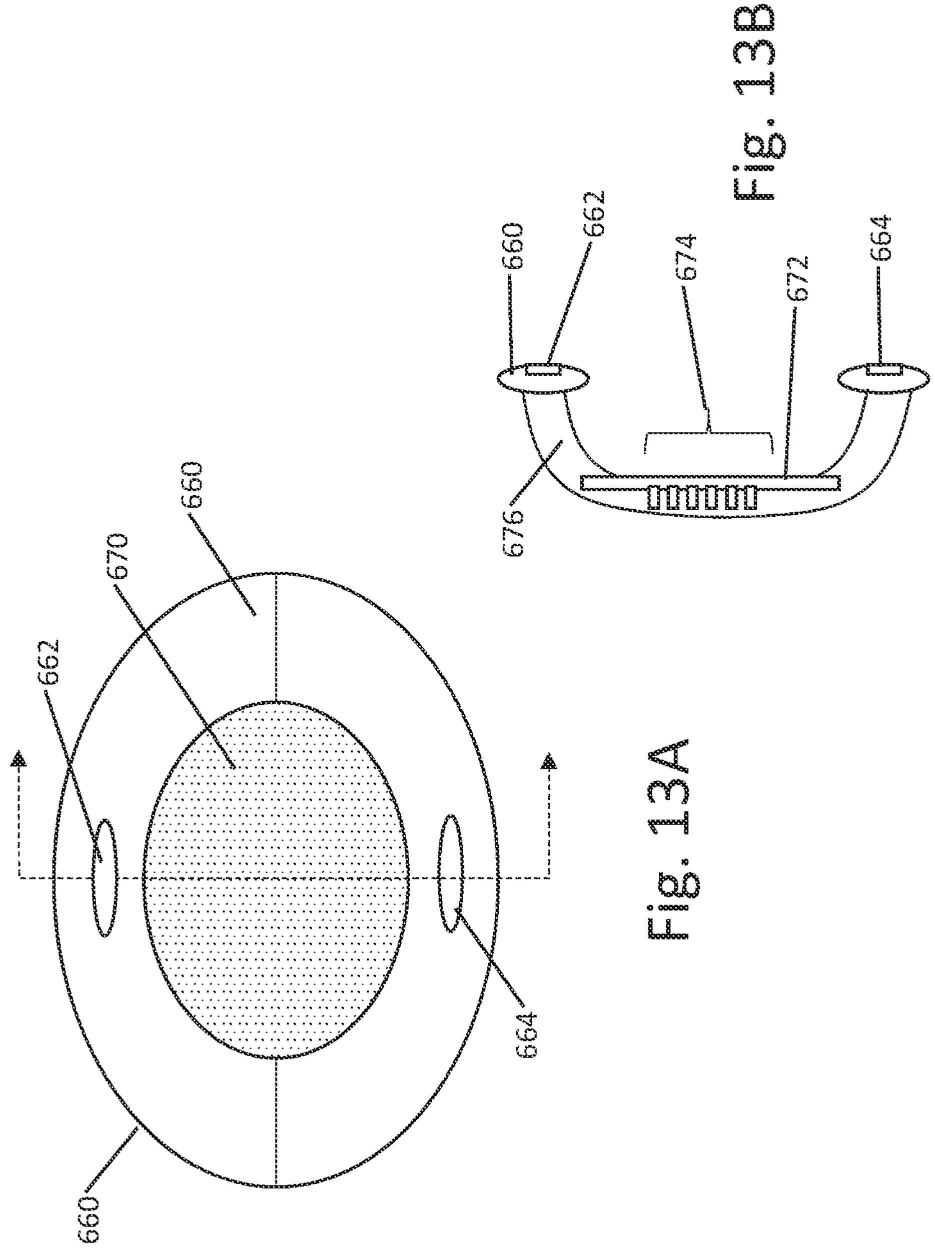

FIGS. 13A-13B show another example. Here, an eyepatch is provided as shown at 650 with a tissue contacting portion 660 and a goggle portion at 670. The tissue contacting portion 660 includes electrodes 662, 664. As shown in the side view of FIG. 13B, the electrodes 662, 664 may conform to the outer surface of the tissue contacting portion 660, such as by having a thin film electrode placed on the surface thereof. For example, the tissue contacting portion may be a two piece element, having a conductive saline therein that passes electrical current to the film electrodes on the surface of an enclosing membrane. Thus each piece, upper and lower, separately electrically links to the electrodes 662 and 664.

Further as shown in FIG. 13B, the goggle portion may contain elements drawn from virtual reality-type goggles, with a view screen 672 and one or more camera element(s) 674. If desired the view screen 672 may be used for entertainment purposes during stimulation delivery. The system may further comprise ear buds, speakers, or headphones again for entertainment purposes. A more medically useful reason for the view screen 672 may be to enable functional vision testing before, during, and/or after therapy delivery. For example, visual acuity testing may be provided by illustrating, for example, letters or shapes. In another example, eye-tracking tests may be performed by having the patient look at a dot on the screen 672 and using the camera element(s) 674 to observe how well the patient tracks to the dot as the dot is moved around on the screen 672. Other functional vision tests may be performed. The rest of the goggle portion 676 may be opaque for purposes of facilitating such testing by blocking ambient light, or may be electrochromatic for the same purpose, if desired. Earbuds, headphones or speakers may also be used to deliver instructions or warnings to the patient during stimulation.

Figure 15:
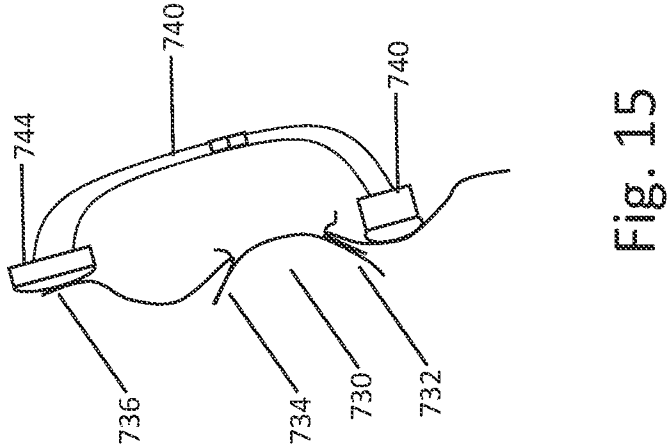
Figure 14:
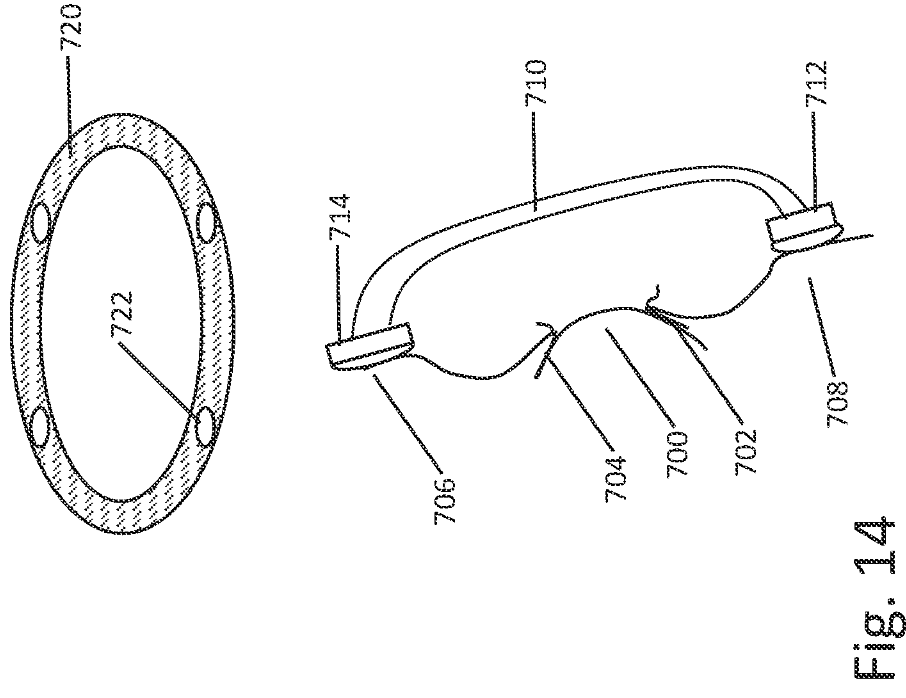

FIGS. 14 and 15 show additional examples, focusing here on tissue contact near the eye. In FIG. 14, the patient is shown with eye 700, beneath a lower lid 702 and upper lid 704. An eyepatch 710 rests on the patient's face, with a lower contact 712 on the cheekbone 708 and the upper contact 714 on the patient's forehead, basically at the eyebrow. The contact positions here are somewhat more distant from the eye, yielding less optimal electrical contact and positioning, as the field is not being applied as close to the eye 700 as possible, however, a benefit here may be comfort in that the patient's eyelids 702, 704 are not contacted, which may be uncomfortable to the patient or may restrict vision significantly. For this example, the tissue contact interface may comprise a replaceable interface pad 702, which may incorporate adhesive therein. Electrodes (not shown) may pass through openings 722 of the pad 702. When the adhesive wears out, the pad may be replaced. In this example, the goggle is shown without any camera or optical elements thereon, which is one of several options, though in other embodiments the various camera, light emitters, and screens noted above may be included.

FIG. 15 shows a different contact approach. Here, the patient's eye is shown at 730 with lower lid 732 and upper lid 734. The eyepatch 740 has a lower contact portion 742 that rests on the lower eyelid 732, and an upper contact portion 744 that again rests against the forehead 736. An advantage here is that the lower contact 742 is now closer to the eye itself, which may enhance the electrical performance. In the example, the approach may be to allow pressure against the forehead 736 while using only a light pressure or adhesive contact against the lower eyelid 732.

Figure 16:
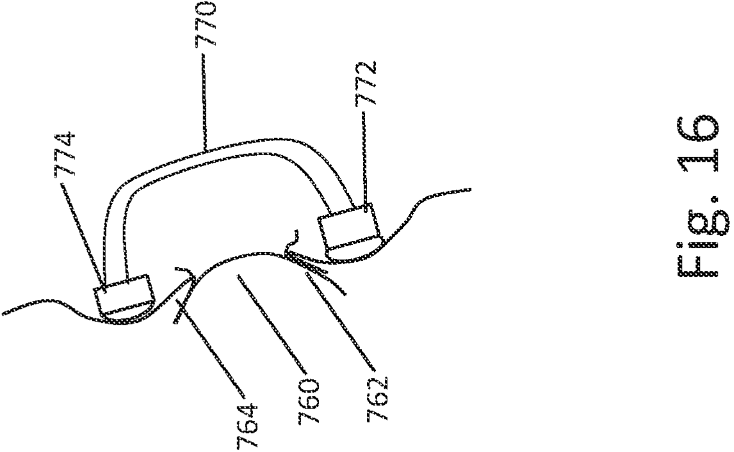

FIG. 16 shows another example. Here, the goggle or eyepiece 770 is placed over the eye 760. A lower contact portion 772 rests against the lower eyelid 762, while an upper contact portion 774 rests against the upper eyelid. For placement on the eye the patient may be instructed to open, or to close, her eyelids as the eyepiece 770 is placed.

Figure 17:
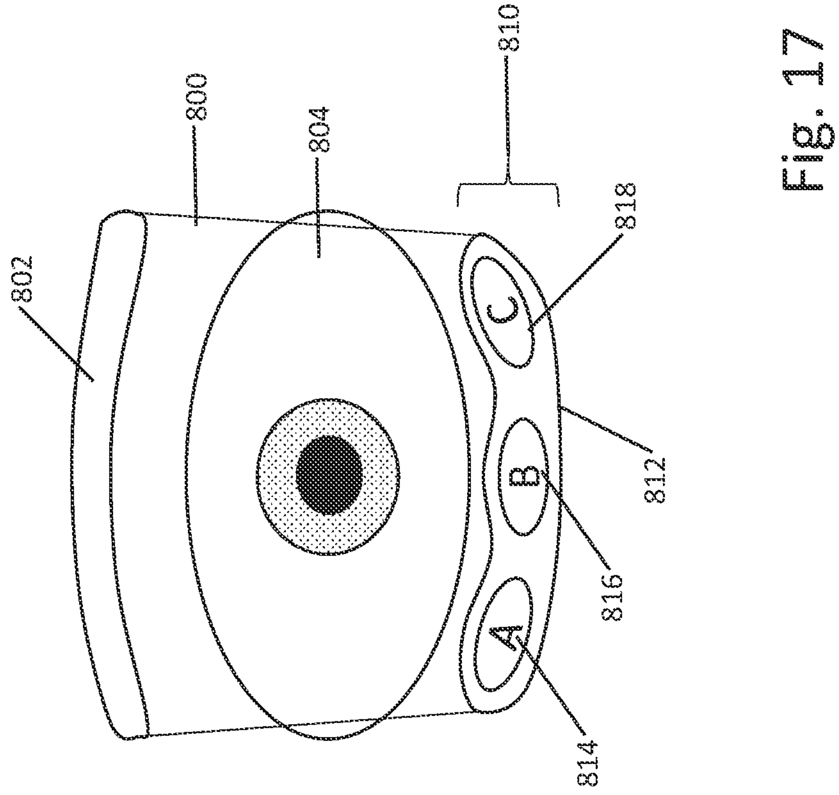

FIG. 17 shows another contact approach using electrodes on the lower eyelid for delivery of ocular modulation therapy. In this example the eyepatch 800 includes a forehead contacting portion 802, a lens, 804, and a lower eyelid contacting portion 810 having an inert portion 812 and three separately addressable electrodes A 814, B, 816, and C 818. In this example, the portions of the apparatus that contact the patient's face are limited to above and below the eye, without attempting to obtain contact at medial and lateral portions of the eye, which may simplify the contact achieved and allow for a single design, or a relatively limited range of designs and sizes (such as 3-5 shapes with 3-5 sizes each, for example), to be used with a variety of patients having different size and shape faces and eyes. In another example, an image of the patient's face may be captured using a camera, and a structure for the tissue interface may be manufactured specific to the patient using, for example, additive or "3D" printing techniques.

One simplification in FIG. 17 is that the forehead contacting portion 802 does not need to have stimulus delivery electrodes therein or thereon. If desired, sensing electrodes, magnetic field generation components, mechanical transducers or the like may be included in the forehead contacting portion 802. The approach therefore simplifies the design for this part of the system. A fold-down mechanism may be used, such as a spring, as shown below in FIGS. 18A-18B, with a system as in FIG. 17. If a spring mechanism is used, the inert region 812 need not be sticky, as pressure will already be applied to attain good skin/electrode contact. The use of three electrodes on portion 810 is illustrative; as few as a single electrode or more than three electrodes may be used if desired.

In this example, the forehead contacting portion 802 may omit stimulation electrodes since such electrodes may be in a less than optimal position for therapy delivery. However, sensing electrodes, such as small needle electrodes or small button electrodes may be used. Such electrodes could be used if desired to sense patient characteristics, such as by electrically monitoring eye movements during therapy or during a visual functional test, or to monitor for neural signals indicating the occurrence of phosphenes during therapy delivery, using methods known in the art. For example, various authors have described testing in rats in which the occurrence of phosphenes is identified by sensing electrical signals. In some examples, smaller cutaneous electrodes, such as having a surface area of a few square millimeters, and which may take the form of dry electrodes and/or capacitive electrodes, may be useful because the smaller area tends to improve signal to noise ratio.

Figures 18A, 18B:
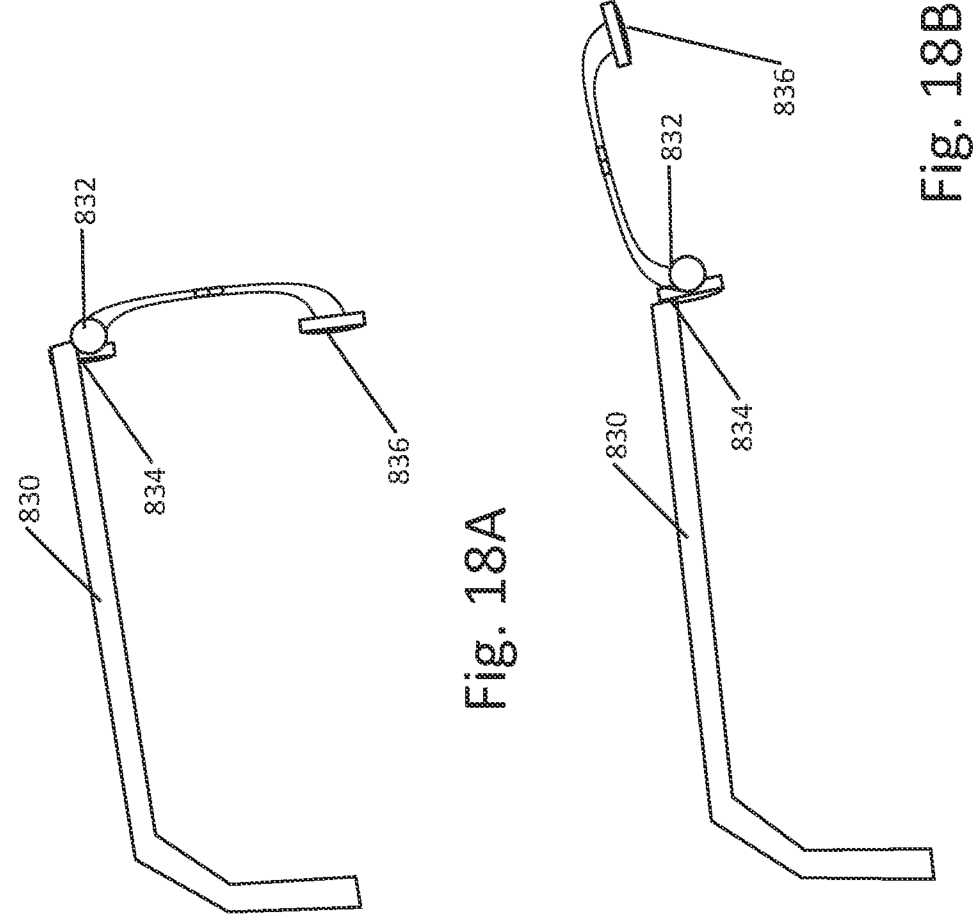

FIGS. 18A-18B show another example for holding an eyepatch on/over the patient's eye. In this example, an eyeglasses-type frame 830 is used, with a front portion comprising a spring 832. The spring 832 may be similar to that used for flip-down sunglasses, having first and second resting positions to preferentially be down as in FIG. 18A, or up as in FIG. 18B. The front portion of the device may rest on the nose of the patient, as with regular glasses and/or it may rest against the forehead of the patient. The position of the forehead contacting portion 834 may be fixed or, as shown in FIG. 18A-18B, may pivot with the rest of the eyepatch. In this example, by adjusting the nose rest of the frame 830 or the forehead contacting portion 834, the lower portion 836 will reliably come into contact with the desired location below the eye, whether on the lower eyelid, or inferior thereto. A return electrode may be placed elsewhere on the patient using any of the designs or positions shown or described above. In an alternative example, the eyeglasses frame 830 may be replaced with a headband, with the spring 832 used to raise or lower the eyepatch.

In use, the patient would don the eyeglasses or headband and get the forehead contacting portion into its desired position before flipping down the eyepatch and lower electrode into stimulation delivery position. The patient may then get everything situated for a therapy session before flipping down the eyepatch, potentially simplifying the process of starting a therapy session. In some examples the act of flipping down the eyepatch may actuate a switch to turn on stimulation, or, in the alternative, the patient may enable the system for stimulation using a switch, a voice command, or a touchscreen, for example. In an example, when the stimulation electrodes are placed into contact with the patient's skin, the sensed impedance or electrical field would change in a detectable and predictable manner, and when such a change in impedance or field is detected, stimulation may begin.

Figures 19, 20A, 20B:
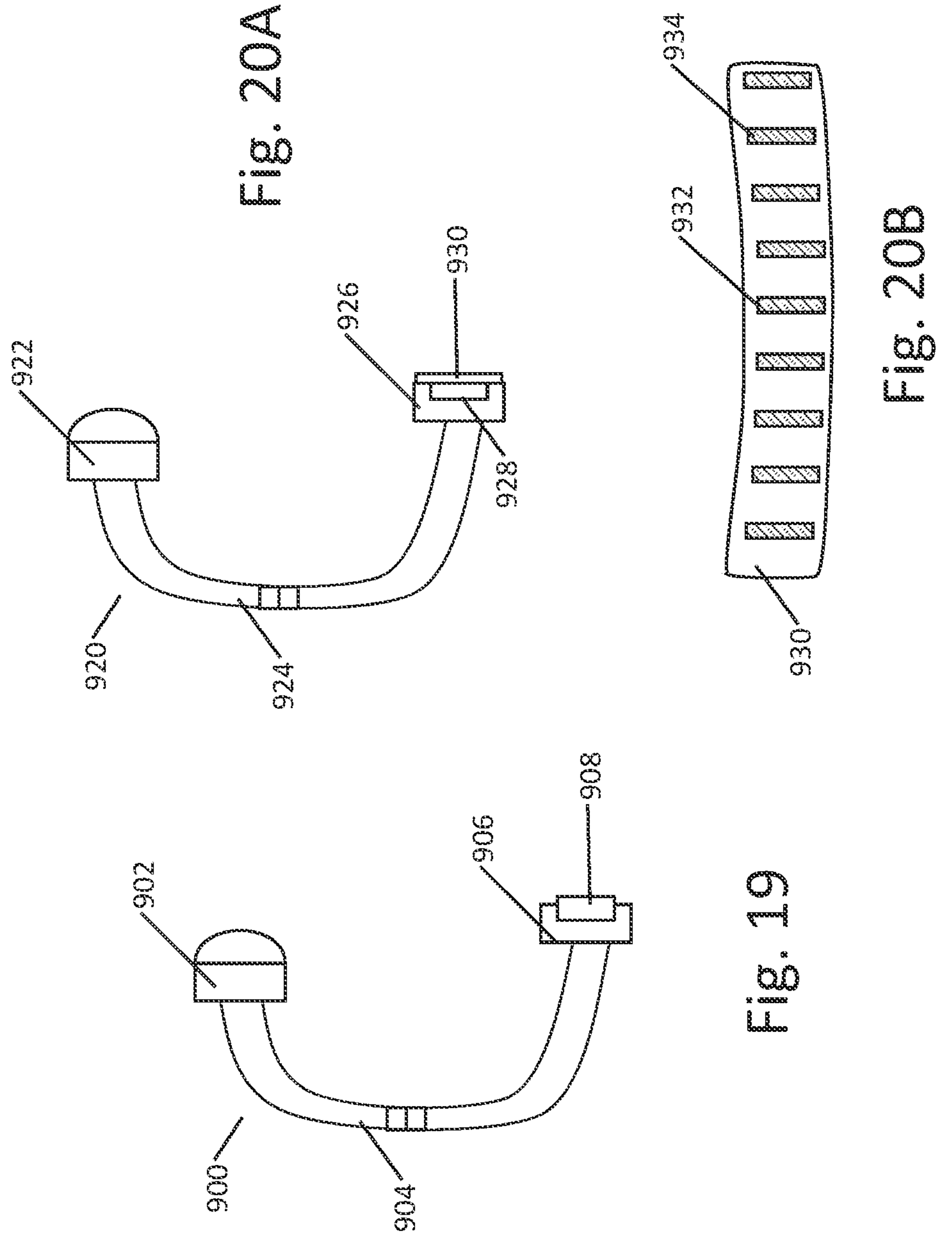

FIGS. 19 and 20A-20B show illustrative examples of asymmetric eyepatches configured to enhance contact. Referring to FIG. 19, the eyepatch 900 comprises an upper contact portion 902, a goggle portion 904, and a lower contact portion 906 having electrode 906; the upper contact portion 902 may be adapted for placement on the forehead or, in the alternative, on the upper eyelid or over the upper fornix of the eyelid. Here, the depth from the front of the goggle portion 904 to the forehead contacting portion 902 is less than the depth to the lower portion 906, which is adapted to contact the lower eyelid or the cheek of the patient. In this example, the electrode 908 is not flush with the surface of the lower portion 906, so that the electrode projects outward to ensure contact with the skin of the patient. In the example, as in any of the other examples herein, any suitable electrode material may be used, including for example, platinum, titanium, gold, stainless steel alloys, tin, silver, silver chloride, aluminum and copper. A coating, such as an oxide layer, may be provided on various such electrodes.

FIGS. 20A-20B shows another example. Here the eyepatch 920 comprises an upper contact portion 922, a goggle portion 924, and a lower contact portion 926 having an electrode 928 and a removeable adhesive element 930. The adhesive element may use a sticky adhesive to provide both adhesion to the patient's skin as well as enhanced conductive contact between the electrode 928 and the patient's skin. In an alternative example, shown FIG. 20B, the adhesive element 930 may include a plurality of sections that create electrical isolation between different electrodes over which the element 930 is placed, as by having alternating conductive portions 932 and adhesive, non-conductive portions 934. The adhesive element 930 may be double sided to adhere on one side to the eyepatch 920 and on the other side to the patient's skin. As the adhesive wears out over time, the adhesive element 930 can be replaced, without requiring replacement of the eyepatch 920 itself.

Figures 20C, 20D:
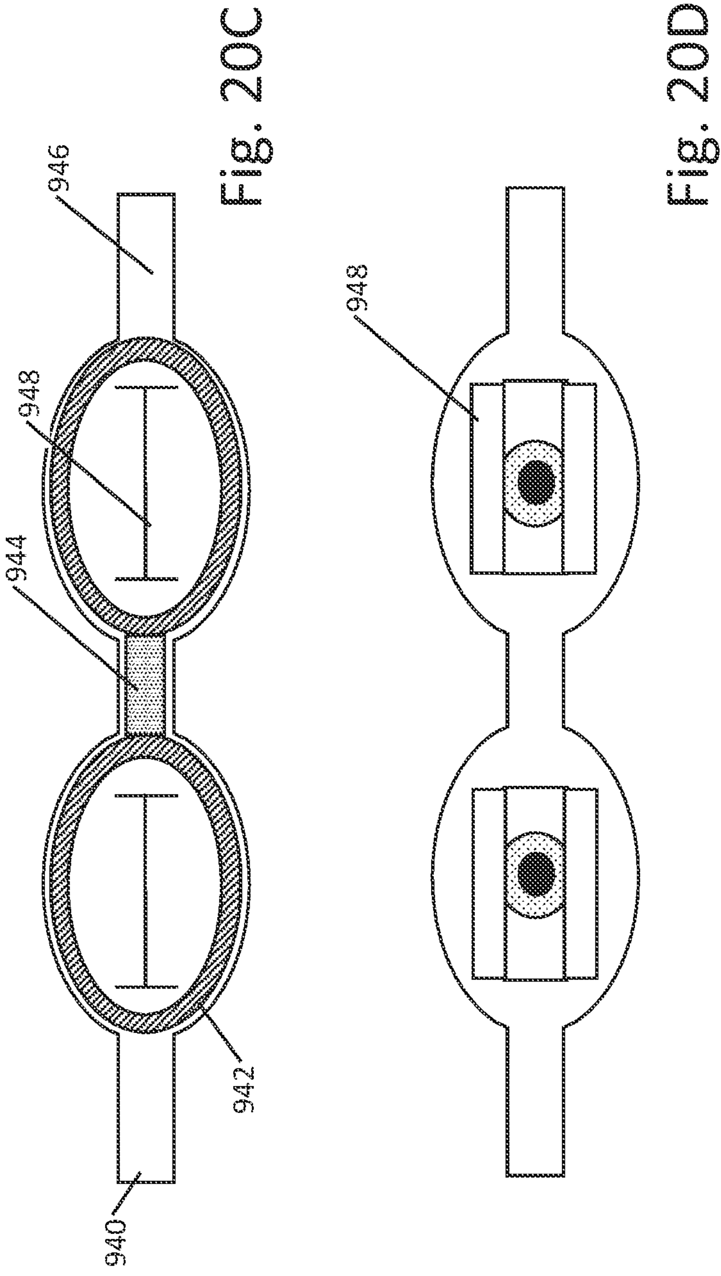

FIGS. 20C-20D illustrate another example in which an eye-mask is used rather than goggles. In FIG. 20C, the eye mask 940 has a conductive region 942 (which may be continuous as shown, or which may be similar to that of FIG. 20B having sections of conductive and non-conductive material), a nose bridge 944, a side band 946, and a cut slit 948. For this example, wires to and from element 942 may be provided in a flex circuit that forms the main body of the mask 940; alternatively, as in FIG. 20B, the eye mask 940 may have conductive portions on both sides thereof, so it can be used with a separate eyepiece carrying stimulus electrodes that couple to the conductive region 942. If desired, the nose bridge 944 may be an adjustable member having a variable length to adapt to various patient anatomies. The eye mask 940 may come in a range of sizes to suit different patient anatomies.

In some examples, the eye mask is applied to a set of goggles and then applied onto the patient. In other examples, the eyemask 940 may carry its own conductors, as already noted. In still other examples, the eyemask 940 may be applied to the patients face first, with an eyepatch as in FIG. 20A, or other designs shown above and below, applied over top. For application to the patient, as shown in FIG. 20D, the cut slit 948 is used to open up and fold back tabs over the patient's eyes, allowing the patient to see out while wearing the mask. In an example, the mask 940 is applied first, to allow the patient to get everything situated before dealing with the wires and pulse generator of the rest of the system. The skin-facing side of the mask shown in FIG. 20C may have adhesive and/or hydrogel over much of its area except in the portions surrounding the cut slit 948. The outward facing side of the eyemask 940 shown in FIG. 20D may have adhesive over all or some of its area, for example to hold the folded-back portions over the eye.

It should be understood that various of the examples shown herein provide illustrations of a single eyepatch. A single eyepatch may be used alone, or may be paired with a second patch of similar construction in any of these examples. For example, if only one eyepatch is provided, the patient may be instructed to use the patch on one eye first and then on the other eye. If a patient has a disease afflicting only one eye, the patient may treat only the afflicted eye.

In any of the examples shown herein, any suitable adhesive may be used, such as adhesive products used on transcutaneous electrical nerve stimulation (TENS) unit pads, or adhesives known for use on cutaneous ECG electrodes, for example. In some examples, a hydrogel may be used. In some examples, the electrode materials may be water vapor impermeable to prevent evaporation of sweat from the patient, thereby adding to the conductivity at the electrode and reducing transcutaneous impedance. The electrode itself may be of any conductive material, whether skin contacting or not, though preferably materials that are non-allergenic (i.e, omitting nickel, in some examples, though nickel may be included in other examples by providing a patient warning and making available both nickel and non-nickel containing electrodes). To preserve adhesive properties the patient may be instructed to wipe skin contact areas prior to a therapy session to remove dirt, cosmetics and oil, for example. In some examples, because an external force is applied using a goggle, headband, or frame, the electrodes may not include an adhesive layer, instead being applied dry, or being applied with a conductive gel, such as a suitable hydrogel, thereon.

Figure 21A:
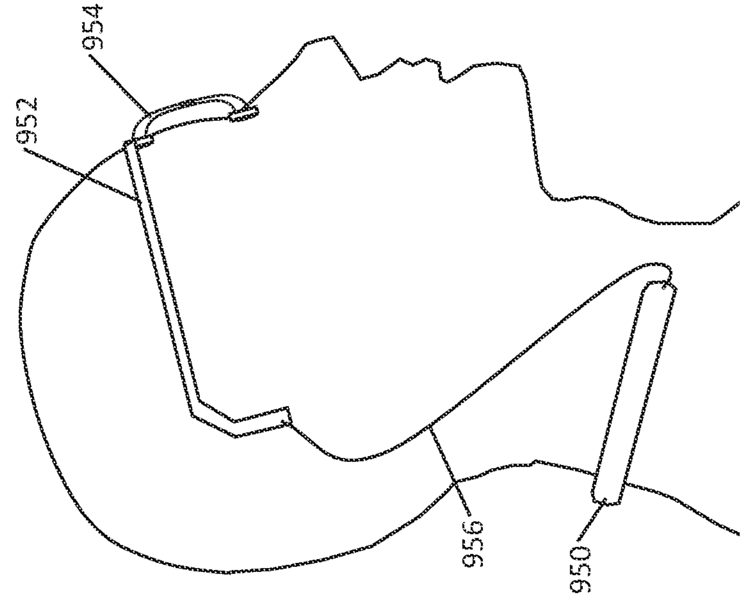
Figure 21B:
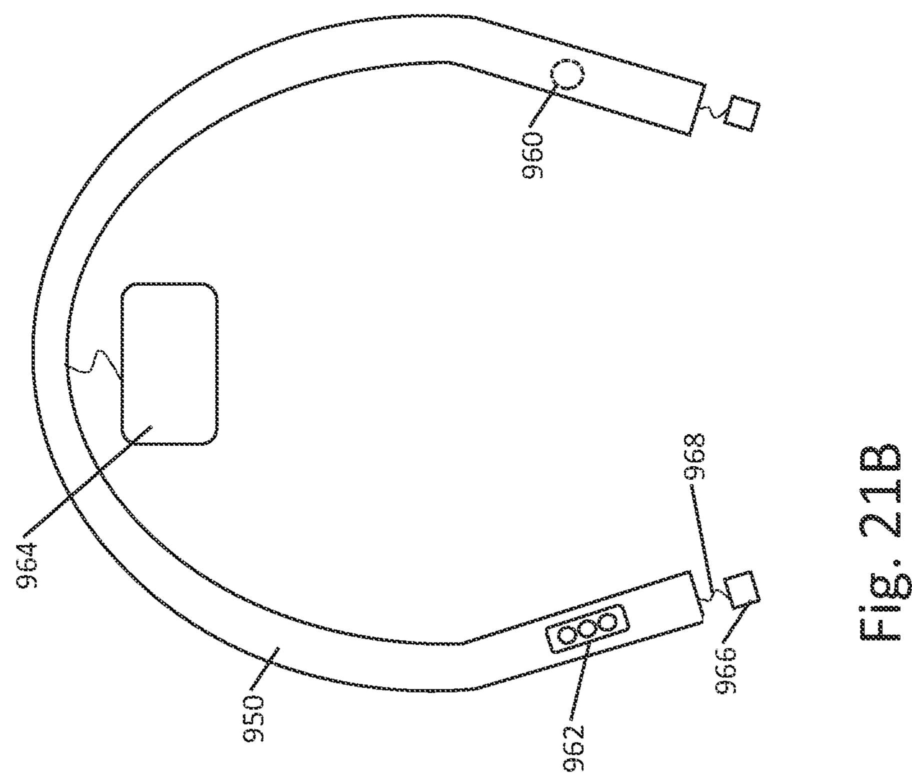
Figure 21C:
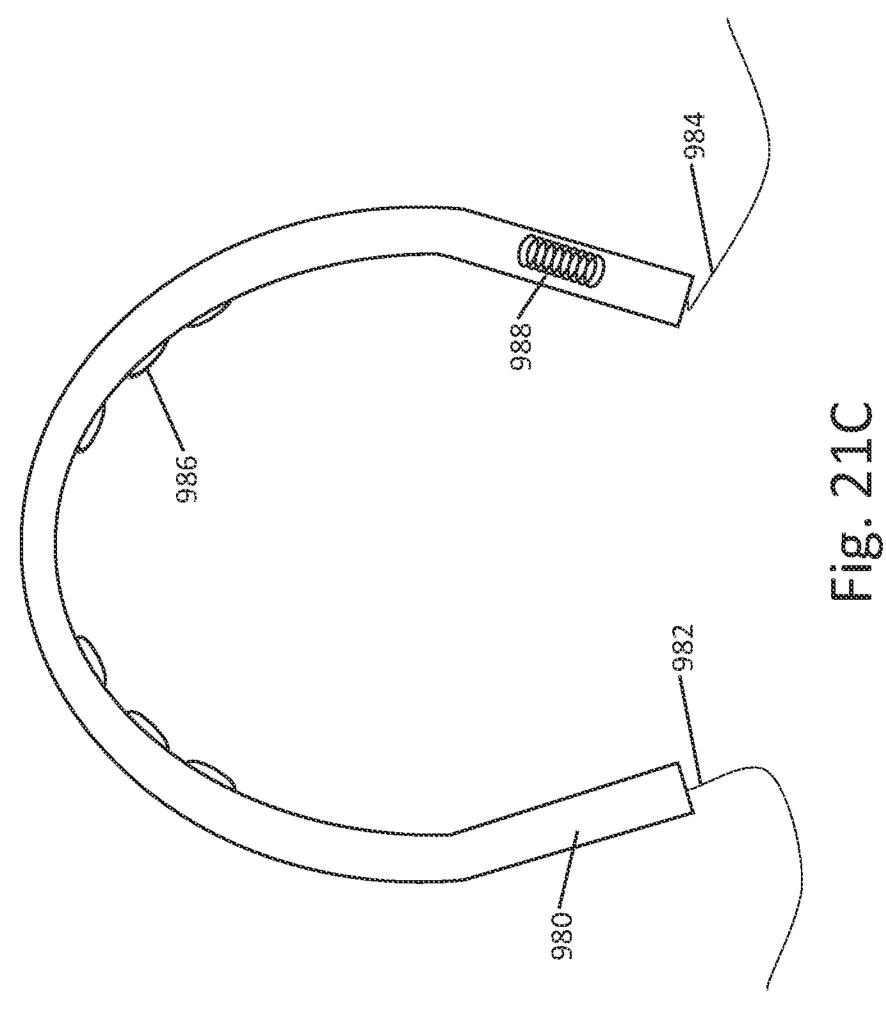

FIGS. 21A-21C show another example. Here, the patient is shown wearing a pulse generator 950 on the neck, with a glasses-type frame 952 holding an eyepatch 954 in position, with a wire connector 956 between the pulse generator 950 and the frame 952. In this example, the pulse generator may comprise an elongated, curved housing generally in the shape of a "U". This may be referred to as a U-shaped pulse generator, but it should be understood that the shape is in reference to the housing and not any particular feature of the electronics (such as a circuit board shape). The pulse generator 950 may contain operational circuitry as described elsewhere herein, such as that in FIG. 23, below.

The patient can wear the housing on the neck, similar to the LG-branded line of Tone headphones which have a housing adapted to be worn on the neck. The pulse generator may contain circuitry as described elsewhere herein, including primary cell or rechargeable battery technology. Electronic components may be distributed in any suitable manner. In one example, which is not intended to be limiting, one "end" of the U-shape contains a power source, such as a battery, and associated recharging circuitry for a rechargeable battery, and/or an associated port structure to allow removal of a non-rechargeable battery, and the other end of the U-shape contains control and output circuitry as well as a structure for receiving a plug in from an associated wearable electrode apparatus, or a retractable electrode, or a retractable cord to attach to an associated wearable electrode apparatus, with electrical connectors and flexible structural components running therebetween to form the central portion of the U-shape. Other arrangements are contemplated.

The wire connector 956 may be detachable from the frame 952 and retractable into the pulse generator 950. In an example, the pulse generator housing may include a return electrode as shown in FIG. 21B at 964. A plug receptacle, which may be multi-pronged, is shown at 962 of FIG. 21B. The plug receptacle may by coupled to a charger for recharging a battery, and/or may be for coupling to a programming device, such as a smartphone, tablet or laptop computer, usable to set parameters for therapy, for example. The plug receptacle may use a special purpose design, or may incorporate a general purpose or universal design, such as a USB-type port (mini-USB, for example), or any other commercially available port type. If desired, headphones or ear buds 966 may be provided as well; Bluetooth functionality may be provided to allow the patient to use the ear buds 966 and a microphone (not shown) for making phone calls during therapy. Rather than ear buds 966, electrodes for application to the patient's skin, such as on the eyelid, may be provided at each end; for example, electrodes may be provided onto which an adhesive shell/patch may be applied for use, where the adhesive patch or shell is adapted to be a single use item that is placed on the electrode before use and then holds the electrode in position adjacent patient skin, directly or via gel interface, for therapy purposes. Such electrodes, much like the ear buds 966, would be extensible from and retractable into the U-shaped housing 950. A recharging port is shown at 960 to allow the pulse generator to be charged for example using an adaptor, a USB port, or any other suitable connector.

The housing for the pulse generator 950 may include one or more metal contact surfaces on an inner portion thereof, which may serve as a return electrode for stimulation delivery. For example, FIG. 21C shows a pulse generator 980 having a plurality of protruding electrodes 986 around at least a portion of its interior surface, such that one or more of the protruding electrodes will be in contact with patient skin during stimulus delivery. In some examples, the pulse generator 950 may be highly flexible and/or tailored or shapeable to conform, at least partly, to the patient's neck. In other examples pulse generator 950 may be less flexible and instead may have plural return electrodes on the inner facing portion thereof usable as return electrodes, with the understanding that least one of the return electrodes would be in contact with the patient's skin at any given time. The return electrode 986 may be covered by, surrounded by, adjacent to, or otherwise associated with a skin adhesive patch to aid in securing to the skin, and/or a gel patch to enhance electrical coupling properties (such as reducing impedance).

The example of FIG. 21C omits the ear buds and instead shows connecting wires 982 and/or 984 that may be used for coupling to an eye patch or set of goggles. Rather than connecting wires, ports may be provided into which couplers associated with an eye patch or set of goggles as disclosed herein can couple. In the example of FIG. 21C, the pulse generator may contain an inductive element 988 that can be used for wirelessly recharging the pulse generator using an inductive charging apparatus. As another alternative, the pulse generator may include a replaceable battery with a lid or cap thereon allowing the battery, such as a standard AAA battery, or several standard hearing aid batteries (or other size or quantity) to be stored during use and replaced when spent. In another alternative, the U-shaped pulse generator may be provided in association with a sleeve carrying an elastic member that connects the two ends of the U-shaped pulse generator to form an encircling structure that the user can wear about the neck, or the pulse generator may include a strap or clasp that closes the open end of the U when worn. A still further alternative may encompass all the details of the U-shaped or neck worn pulse generator described herein in a fully encircling pulse generator housing which can be worn about the neck of the patient as a collar or necklace. The U-shape form may be easier for the user to remove and don, particularly for the user of limited visual capability. A fully encircling pulse generator may, on the other hand, stay in place so that the user does not have to find it again once removed.

A neck-worn pulse generator as in any of FIGS. 21A-21C may be permanently wired to signal delivery electrodes for issuing therapy to a patient's eye or eyes, or may have, as noted, one or more ports for receiving electrical connectors (such as couplers or plugs) that electrically connect to such signal delivery electrodes. The signal delivery electrodes, which can be permanently or removably coupled to the neck-worn pulse generator, may be provided on or held in place by a frame or headband and/or other structures disclosed herein, or on an eyepiece, goggles, or other structure (including nasal electrodes, wet electrodes, and/or conjunctiva electrodes) as disclosed in any of U.S. Provisional Patent Applications No. 62/832,134, filed Apr. 10, 2019, titled SYSTEMS AND INTERFACES FOR OCULAR THERAPY, No. 62/861,658, filed Jun. 14, 2019 and titled WEARABLE MEDICAL DEVICE, No. 62/867,421, filed Jun. 27, 2019, titled SYSTEMS AND INTERFACES FOR OCULAR THERAPY, No. 62/873,450, filed Jul. 12, 2019 and titled OCULAR THERAPY MODES AND SYSTEMS, No. 62/884,890, filed Aug. 9, 2019 and titled WEARABLE MEDICAL DEVICE, and U.S. patent application Ser. No. 16/589,383, filed Oct. 1, 2019, the disclosures of each of which are incorporated herein by reference.

In a method of treating a patient having an eye disease, the method may comprise a patient donning a neck-worn pulse generator 950 containing operational circuitry including output circuitry configured to generate output electrical pulses and a patient donning a plurality of stimulus delivery electrodes electrically coupled to the pulse generator and adapted, when worn by a patient, to deliver stimulus generated using the output circuitry to at least one eye of the patient. The patient may do so by applying any of the electrode assemblies or types as described in the immediately preceding paragraph, including those of the incorporated patent applications. Next, the method can continue with the patient activating the pulse generator to deliver a stimulus to the eye of the patient, and the pulse generator issuing stimulus to the eye. The stimulus may be automatically delivered, or, instead, in response to the patient activation, the pulse generator may test impedance between one or more pairs of stimulus delivery electrodes to confirm appropriate contact with patient tissue and, in response to confirming appropriate contact with patient tissue, the pulse generator issues the stimulus to the eye, using for example, methods of testing impedance and tissue contact discussed herein and/or in U.S. patent application Ser. No. 16/589,383. As noted, the pulse generator 950 may comprise at least one return electrode thereon for use as a return or indifferent electrode when output electrical pulses are generated, such that the step of the pulse generator issuing stimulus to the eye may, for at least some stimulus delivery, use the at least one electrode on the pulse generator as a return or indifferent electrode. In addition, in the use example, the pulse generator is U-shaped, and the pulse generator comprises at least one retractable wire carrying at least one of the stimulus delivery electrodes thereon, such that the step of the patient donning the stimulus delivery electrodes comprises extending the retractable wire from the pulse generator. Such use steps (except for the U-shape element) may be applicable as well to the other forms for pulse generators described herein, including those carried on headbands and frames or carried elsewhere on the body.

Figure 22:
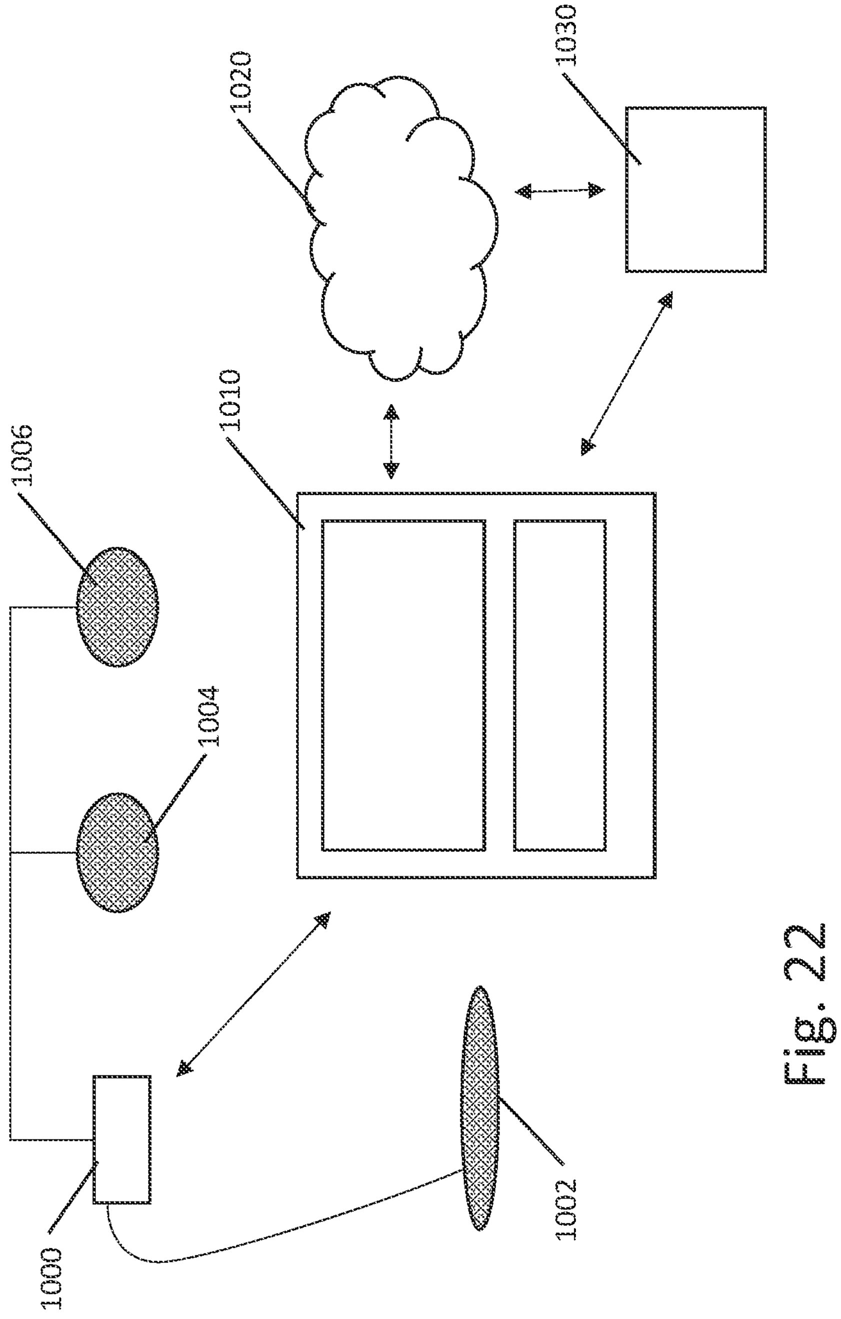
FIG. 22 shows an overall treatment system.

FIG. 22 shows an overall system and network for providing ocular modulation therapy. A pulse generator 1000 is connected to a return electrode 1002 and eyepatches 1004, 1006. The pulse generator 1000 includes communication circuitry, such as an antenna and driver circuitry therefore which adapted for WiFi, MedRadio, WLAN, Bluetooth, cellular, or other communications modality.

In some examples, a patient communicator 1010 may be provided for communicating with the pulse generator 1000. In some examples, the patient communicator 1010 may be a dedicated device specifically designed for use with pulse generator 1000 by a manufacturer, similar, for example, to the Carelink remote monitoring systems offered by Medtronic. In other examples, the patient communicator 1010 takes the form of a multipurpose smartphone, tablet, or laptop computer that is the patient's own device, or which may be provided to a patient, having an application or executable program to allow control of the pulse generator 1000 and which retrieves stimulation and diagnostic information from the pulse generator 1000. The patient communicator 1010 may therefore include suitable communication circuitry corresponding to that of the pulse generator 1000 to facilitate communication such as by WiFi, MedRadio, WLAN, Bluetooth, cellular, or other communications modality. The communication may be mediated by a network or tower, or may be direct.

The patient communicator 1010 may include cellular or other communications technology to allow information to be uploaded for example to a cloud server 1020 or directly to a physician counterpart device 1030. The physician device 1030 may be, for example, a dedicated product or a multipurpose smartphone, tablet, or laptop computer that includes an application or executable program to allow a user to access information from the pulse generator 1000 and/or patient communicator 1010 to analyze patient status, stimulation history or usage, and/or whether the system is in working condition and/or is being properly used. The physician device 1030 may pull information from the cloud server 1020 or directly from the patient communicator 1010 for such purposes.

In some examples, the patient communicator 1010 may be omitted, and the pulse generator 1000 can be remotely programmed by the physician device 1030. In some such examples, and as also disclosed above, the pulse generator 1000 may be adapted to automatically turn on and deliver stimulus when the patient is wearing one or more of the eyepatches 1004, 1006 and return electrode 1002. In other examples, the patient communicator 1010 may be used to allow the patient to turn stimulus on or off, or to allow the patient to enter information (such as by answering queries from the physician or automatically generated queries) that the physician may find useful.

Various additional details for the design and use of a system and components thereof as shown in FIG. 22 may be found in U.S. patent application Ser. No. 16/589,383, filed Oct. 1, 2019, the disclosure of which is incorporated herein by reference.

Figure 23:
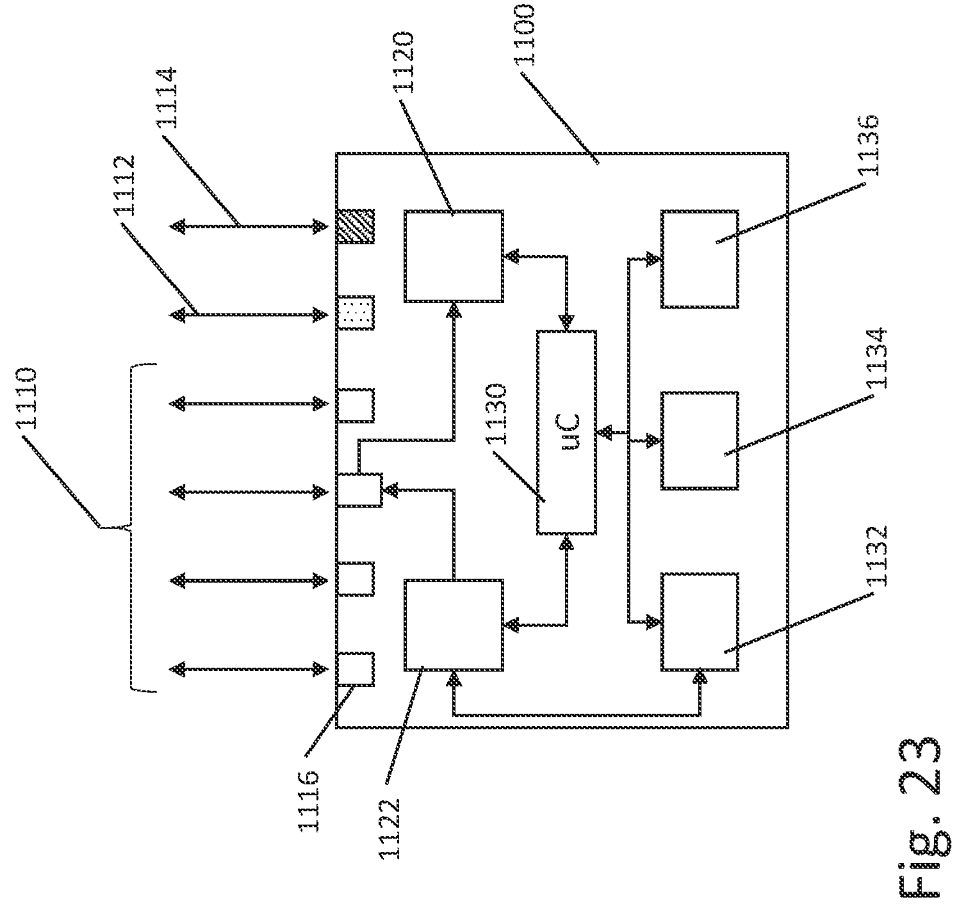
FIG. 23 shows an illustrative pulse generator.

FIG. 23 shows an illustrative pulse generator at 1100. The pulse generator 1100 includes a number of outputs, which may include electrical stimulus outputs 1110 and, optionally one or more non-stimulus inputs or outputs 1112, 1114. The stimulus outputs 1110 are illustratively shown as including four separate channels; more or fewer channels may be provided. In an illustrative example, a system includes output circuitry for delivering electrical stimuli to the eye of a patient. The output circuitry may include one or more output channels, operable independently to provide greater control over current output than is possible with a single output channel. By controlling output across more channels, the resultant field can be controlled in a manner that allows the physician to tailor therapy to the particular patient's anatomy. For example, shaping the developed field to ensure coverage of the therapeutic target can be better facilitated with a plurality of output channels. 2, 3, 4 or more channels for output currents may be provided. Other examples may have a single channel output.

Therapy parameters directed to ocular therapy, including for example therapy parameters that may be used in delivering therapy to the retina and/or macula are also disclosed in U.S. patent application Ser. No. 16/589,383, the disclosure of which is incorporated herein by reference. In some examples, an output of less than one volt, or less than one milliamp of controlled current, may be provided, with a pulse rate in the range of 0.05 Hertz up to as much as 20,000 Hertz, or 0.1 Hertz up to 1,000 Hertz. In some examples, the pulse rate may be up to 300 Hz, or in the range of 10 to 30 Hz. Outputs may be in the range of 100 nanoamps, or 100 nanowatts, or 100 nanovolts, or lower, if desired, up to the range of microamps, microwatts, or microvolts, or up to the range of milliamps, milliwatts, or millivolts, or higher. In some examples, the impedance encountered may call for voltage or power to exceed 1 volt and/or 1 watt, though current in many cases will remain well below 1 amp. In an example, the maximum current may be 10 milliamps. In some examples, voltage may be as high as 1 volt, or as high as 50 volts. The duty cycle of any therapy output may be controlled as well, for example, between 10% to 100% duty cycle may be use. Pulse widths of as short as a few nanoseconds, for example as short as 10 nanoseconds, up to 1 second, or more or less, may be used; in some examples, the pulse width is defined in a microsecond range, for example, between 10 and 100 microseconds. In other examples, a millisecond level pulse width may be used, such as between 1 and 100 milliseconds, for example, 10 milliseconds, delivered at 10 to 30 Hz. In some examples, a square wave or sinusoidal wave, or other waveshape, is delivered at a repetition rate. In other examples, a burst pattern is used by delivering a first, higher frequency signal (such as a 10 kilohertz square wave) in an envelope defined by a second, lower frequency signal (such as a signal of less than 1 kilohertz, or in the range of 0.3 to 300 Hertz).

The non-electrical-stimulus inputs or outputs 1112, 1114 may deliver electrical, optical, or mechanical energy for therapy or diagnostic purposes. For example, output 1112 may deliver electrical signals that drive a laser diode used for illuminating or stimulating the patient's eye, while input 1114 may receive electrical signals from a camera that captures images of the retina or other eye structures while the laser diode illuminates a target anatomical structure. Temperature may be monitored via one of 1112, 1114 in another example. Inputs/outputs 1112, 1114 may be omitted in some examples, while in other examples, more than two such inputs/outputs 1112, 1114 may be provided. Mechanical (i.e. vibrational, such as ultrasound) energy may be transmitted from a transducer in the pulse generator 1100, or an electrical signal to drive such a transducer that is located on an eyepiece may be provided in some examples. In some examples, rather than issuing electrical therapy on some signal lines and not others, all the outputs may be adapted for non-electrical therapy purposes, and instead drive transducers for generating mechanical, magnetic, or optical stimulus, if desired.

Filtering or DC blocking circuitry may be provide as indicated at 1116 for each of the inputs/outputs, as desired and suitable. In the example shown, the pulse generator 1100 may include a sensing circuit 1120, which may include suitable filtering, amplification and (optionally) analog to digital conversion circuitry to allow signals to be sensed such as to facilitate measuring voltages during stimulus delivery in order to measure electrode impedance of active electrodes or to capture electrical fields from inactive electrodes, as described above. A stimulus output circuit 1122 is also shown, and may include appropriate driving circuitry such as digital to analog conversion circuitry, amplifiers, and the like, as are known in the art for generating voltage or current controlled stimulus. In an example, stimulation may be delivered by charging a capacitor to a desired voltage level and then discharging it. In another example, one or more current mirrors are used, with one circuit path providing a control signal while other circuit paths match the control signal to generate a current controlled output. Other driving circuitry known in the art may be used in addition or instead.

The illustrative pulse generator 1100 may include, if desired, a microcontroller 1130. Alternatively, a state machine, microprocessor, field programmable gate array, or application specific integrated circuit may be used to control the overall operation of the system. Additional blocks 1132, 1134, 1136 may comprise, for example, a power source, power management, communication, user interface, and/or memory circuitry. A power source may take the form of a rechargeable or non-rechargeable battery, or a supercapacitor, or any other suitable power supply. Power management may comprise up-converting or down-converting circuits adapted to take the output of the power supply and provide suitably controlled voltage or current for use by the rest of the system; for example, power management may comprise a capacitor and inductor, or a switched capacitor network, to provide a compliance voltage that is higher than the battery voltage for use by a constant current output circuit. A communication circuit may comprise an antenna, or be coupled to an antenna, and include driver circuitry for WiFi, MedRadio, WLAN, Bluetooth, cellular, or other communications modality. For pulse generators that are adapted to plug into a system controller, such as a computer (laptop, desktop or table) or smartphone, the communication circuit may include elements for passing power through to the power source (if rechargeable) as well as circuitry to receive wired communications through such a plug-in interface (i.e. a USB port of any type, such as Mini-USB, USB-A, etc. or other standard or non-standard and/or proprietary wired connection). A user interface may include one or more buttons, switches, a screen, a touchscreen, a speaker or microphone, a buzzer, LED lights or the like, a keyboard, or any other suitable input or output device to enable a patient to receive instructions or information about device operation and/or to control the device. Memory circuitry may include, for example, flash memory, read only memory or any suitable circuit that can store information for retrieval, such as a non-transitory medium for storing instruction sets for execution by the microcontroller 1130, as well as to store diagnostic information, such as measured impedances, and stimulation history.

Additional details regarding power storage, including battery types, size, such as volume or mass, as well as examples of potential power demand of an illustrative system described, without limiting the present invention to such designs, as well as further eyepiece and electrode designs, in U.S. Provisional Patent Application No. 62/832,134, filed Apr. 10, 2019, titled SYSTEMS AND INTERFACES FOR OCULAR THERAPY, the disclosure of which is incorporated herein by reference. Still further examples for interfacing with tissue near the eye, as well as pulse generator designs, power concepts and circuitry, are described in U.S. Provisional Patent Application No. 62/867,421, filed Jun. 27, 2019, titled SYSTEMS AND INTERFACES FOR OCULAR THERAPY, and 62/873,450, filed Jul. 12, 2019 and titled OCULAR THERAPY MODES AND SYSTEMS, the disclosures of which are incorporated herein by reference.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A patient interface apparatus for delivery of stimulus to a portion of the head of a patient for a session, the patient interface apparatus comprising:

a first eyepiece adapted to fit about at least one eye of the patient;

wherein the first eyepiece comprises at least first and second electrodes, the first eyepiece further comprising at least first and second electrical connectors separately coupled to the first and second electrodes;

wherein the patient interface apparatus further comprises a pulse generator coupled to at least the first and second electrical connectors to issue electrical therapy pulses using the first and second electrodes; and wherein the pulse generator is configured to:

monitor a tissue impedance between the first and second electrodes before commencement of the electrical therapy to establish an initial impedance-based threshold for the patient;

define a session-specific acceptable impedance upper limit on the basis of the initial threshold;

compare a subsequently monitored tissue impedance to the session-specific acceptable impedance upper limit; and interrupt or withhold the electrical therapy when the subsequently monitored tissue impedance exceeds the session-specific acceptable impedance upper limit.

2. The patient interface apparatus of claim 1, further comprising a frame or a strap to hold the first eyepiece on the head of the patient, wherein the first eyepiece is configured to hold the first electrode on the patient's eyelid.

3. The patient interface apparatus of claim 1 wherein the first eyepiece is a closed eyepiece having a transparent portion through which the patient can see while wearing the first eyepiece.

4. The patient interface apparatus of claim 1, wherein the pulse generator is configured to issue therapy pulses by using the first and second electrodes of the first eyepiece as opposing electrodes.

5. The patient interface apparatus of claim 4, wherein the first and second electrodes are positioned on the eyepiece above and below the transparent portion.

6. The patient interface apparatus of claim 4, wherein the first and second electrodes are positioned on the eyepiece below the transparent portion.

7. The patient interface apparatus of claim 4, wherein the pulse generator is configured to issue the therapy pulses using the first and second electrodes of the first eyepiece as opposing electrodes without a separate return electrode.

8. The patient interface apparatus of claim 1, further comprising a second eyepiece adapted to fit about at least one eye of the patient and including at least third and fourth electrodes, the second eyepiece further comprising at least third and fourth electrical connectors separately coupled to the third and fourth electrodes, wherein the pulse generator is coupled to the third and fourth electrical connectors to issue therapy pulses from the third and fourth electrodes.

9. The patient interface apparatus of claim 8, wherein the pulse generator is configured to issue therapy pulses using the first and second electrodes together as one of anode or cathode, and using the third and fourth electrodes together in electrical opposition to the first and second electrodes.

10. A method of treating a patient having a vision disorder comprising:

having the patient wear a patient interface apparatus for a session comprising:

(i) a first eyepiece adapted to fit about at least one eye of the patient, wherein the first eyepiece comprises at least first and second electrodes, the first eyepiece further comprising at least first and second electrical connectors separately coupled to the first and second electrodes, and (ii) a pulse generator coupled to at least the first and second electrical connectors to issue therapy pulses using the first and second electrodes; and activating the pulse generator to issue an electrical therapy to the eye using the first and second electrodes as a series of electrical therapy pulses;

monitoring a tissue impedance between the first and second electrodes before commencement of the electrical therapy to establish an initial impedance-based threshold for the patient;

defining a session-specific acceptable impedance upper limit on the basis of the initial threshold;

comparing a subsequently monitored tissue impedance to the session-specific acceptable impedance upper limit; and interrupting or withholding the electrical therapy when the subsequently monitored tissue impedance exceeds the session-specific acceptable impedance upper limit.

11. The method of claim 10, wherein the patient interface apparatus further comprises a frame or a strap to hold the first eyepiece on the head of the patient, and wherein the first eyepiece is a closed eyepiece having a transparent portion through which the patient can see while wearing the first eyepiece and receiving electrical therapy.

12. The method of claim 10, wherein the step the pulse generator issuing the electrical therapy comprises the pulse generator using the first and second electrodes of the first eyepiece as opposing electrodes.

13. The method of claim 12, wherein the first and second electrodes are positioned above and below the eye.

14. The method of claim 12, wherein the first and second electrodes are positioned below the eye.

15. The method of claim 12, wherein the pulse generator using the first and second electrodes of the first eyepiece as opposing electrodes is performed without the use of a separate return electrode.

16. The method of claim 10, wherein the patient interface apparatus includes a second eyepiece adapted to fit about at least one eye of the patient and including at least third and fourth electrodes, the second eyepiece further comprising at least third and fourth electrical connectors separately coupled to the third and fourth electrodes, wherein the pulse generator is coupled to the third and fourth electrical connectors to issue therapy pulses from the third and fourth electrodes.

17. The method of claim 16, wherein the step of the pulse generator issuing the electrical therapy as a series of electrical therapy pulses comprises using the first and second electrodes together as one of anode or cathode, and using one or more return electrodes in electrical opposition to the first and second electrodes.

18. The patient interface apparatus of claim 1, further comprising one or more return electrodes.

19. The patient interface apparatus of claim 18, wherein the one or more return electrodes are coupled to an earpiece of the frame.

20. The patient interface apparatus of claim 18, wherein the impedance of the at least one of the first and second electrodes is measured relative to the one or more return electrodes.

21. The patient interface apparatus of claim 20, wherein the pulse generator is further configured to determine tissue-electrode contact quality by selectively enabling one of the first and second electrodes while disabling the other, and measuring impedance between the enabled electrode and the one or more return electrodes.

22. The patient interface apparatus of claim 20, wherein the pulse generator is configured to perform differential impedance measurements by measuring impedance between each of the first and second electrodes and the one or more return electrodes, and comparing the measured impedances to one another to identify which electrode has inadequate tissue contact.

23. The patient interface apparatus of claim 20, wherein the pulse generator is configured to confirm tissue contact at the first and second electrodes by performing localized impedance tests between the first and second electrodes without referencing the one or more return electrodes, and using results of the localized impedance tests in conjunction with impedance measurements relative to the one or more return electrodes to distinguish whether high impedance is caused by one of the first and second electrodes or by the one or more return electrodes.

24. The patient-interface apparatus of claim 20, further comprising a third electrode, wherein the pulse generator is configured to deliver a diagnostic test stimulus between at least one of the first and second electrodes and the one or more return electrodes while sensing an electrical response at the third electrode to determine tissue-electrode contact quality prior to or during the electrical therapy.

25. The patient-interface apparatus of claim 1, wherein the pulse generator is configured to deliver a low-amplitude diagnostic pulse, distinct from the electrical therapy pulses, to obtain the initial tissue-impedance measurement and to refrain from issuing the electrical therapy pulses until the measured tissue impedance is below the session-specific acceptable impedance upper limit.

26. The patient-interface apparatus of claim 1, wherein the pulse generator is further configured to monitor the tissue impedance at predetermined intervals during the sequence of electrical therapy pulses, dynamically update the session-specific acceptable impedance upper limit in accordance with changes in the monitored impedance, and interrupt the electrical therapy when the monitored impedance falls outside the updated upper limit.

27. The patient-interface apparatus of claim 1, wherein the pulse generator is configured to: define a session-specific acceptable impedance range including the upper limit on the basis of the initial threshold; compare a subsequently monitored tissue impedance to the session-specific acceptable impedance range; and interrupt or withhold the electrical therapy when the subsequently monitored tissue impedance lies outside the session-specific acceptable impedance range.

28. The patient-interface apparatus of claim 1, wherein the pulse generator is further configured to determine if the initial threshold is within an acceptable range.

29. The patient interface apparatus of claim 1, wherein the pulse generator is configured to issue therapy pulses using the first and second electrodes together as one of anode or cathode, and using one or more return electrodes in electrical opposition to the first and second electrodes.

* * * * *